United States Patent
Chen et al.

(10) Patent No.: US 9,512,444 B2
(45) Date of Patent: Dec. 6, 2016

(54) GENOME EDITING USING TARGETING ENDONUCLEASES AND SINGLE-STRANDED NUCLEIC ACIDS

(75) Inventors: Fuqiang Chen, St. Louis, MO (US); Shondra M. Pruett-Miller, St. Louis, MO (US); Gregory D. Davis, St. Louis, MO (US)

(73) Assignee: Sigma-Aldrich Co. LLC, St. Louis, MO (US)

(*) Notice: Subject to any disclaimer, the term of this patent is extended or adjusted under 35 U.S.C. 154(b) by 168 days.

(21) Appl. No.: 13/811,884

(22) PCT Filed: Jul. 22, 2011

(86) PCT No.: PCT/US2011/045037
§ 371 (c)(1),
(2), (4) Date: Feb. 11, 2013

(87) PCT Pub. No.: WO2012/012738
PCT Pub. Date: Jan. 26, 2012

(65) Prior Publication Data
US 2013/0137180 A1    May 30, 2013

Related U.S. Application Data

(60) Provisional application No. 61/367,022, filed on Jul. 23, 2010, provisional application No. 61/382,965, filed on Sep. 15, 2010, provisional application No. 61/410,124, filed on Nov. 4, 2010.

(51) Int. Cl.
C12N 15/90 (2006.01)
C12N 15/85 (2006.01)
C12N 9/22 (2006.01)

(52) U.S. Cl.
CPC ............. *C12N 15/85* (2013.01); *C12N 9/22* (2013.01); *C12N 15/907* (2013.01)

(58) Field of Classification Search
None
See application file for complete search history.

(56) References Cited

U.S. PATENT DOCUMENTS

| | | | |
|---|---|---|---|
| 5,352,660 A | 10/1994 | Pawson | |
| 5,356,802 A | 10/1994 | Chandrasegaran | |
| 5,420,032 A | 5/1995 | Marshall et al. | |
| 5,436,150 A | 7/1995 | Chandrasegaran | |
| 5,487,994 A | 1/1996 | Chandrasegaran | |
| 5,667,980 A | 9/1997 | Pawson et al. | |
| 5,789,538 A | 8/1998 | Rebar et al. | |
| 5,814,466 A | 9/1998 | Pawson | |
| 5,925,523 A | 7/1999 | Dove et al. | |
| 6,007,988 A | 12/1999 | Choo et al. | |
| 6,013,453 A | 1/2000 | Choo et al. | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,495,664 B1 | 12/2002 | Cubitt | |
| 6,534,261 B1 | 3/2003 | Cox, III et al. | |
| 6,607,882 B1 | 8/2003 | Cox, III et al. | |
| 6,833,252 B1 | 12/2004 | Dujon et al. | |
| 6,903,185 B2 | 6/2005 | Kim et al. | |
| 7,153,949 B2 | 12/2006 | Kim et al. | |
| 7,192,772 B1 | 3/2007 | Ingram et al. | |
| 7,314,712 B2* | 1/2008 | Storici et al. ............... 435/6.14 |
| 7,332,589 B2 | 2/2008 | Kubota et al. | |
| 2002/0004491 A1 | 1/2002 | Xu et al. | |
| 2002/0119570 A1 | 8/2002 | Yoon et al. | |
| 2003/0232410 A1 | 12/2003 | Liljedahl et al. | |
| 2004/0009479 A1 | 1/2004 | Wohlgemuth et al. | |
| 2004/0019002 A1 | 1/2004 | Choulika et al. | |
| 2004/0219523 A1 | 11/2004 | Stanton et al. | |
| 2005/0026157 A1 | 2/2005 | Baltimore et al. | |
| 2005/0064474 A1* | 3/2005 | Urnov et al. .................... 435/6 |
| 2005/0208489 A1 | 9/2005 | Carroll et al. | |
| 2006/0063231 A1 | 3/2006 | Li et al. | |
| 2006/0171929 A1 | 8/2006 | Clark et al. | |
| 2006/0188987 A1 | 8/2006 | Guschin et al. | |
| 2006/0199226 A1 | 9/2006 | Schiffer | |
| 2006/0211075 A1 | 9/2006 | Lawrence et al. | |
| 2007/0134796 A1 | 6/2007 | Holmes et al. | |
| 2007/0155014 A1 | 7/2007 | Bertolini et al. | |
| 2007/0218528 A1 | 9/2007 | Miller | |
| 2007/0298973 A1 | 12/2007 | Anderson et al. | |
| 2008/0131962 A1 | 6/2008 | Miller | |
| 2008/0159996 A1 | 7/2008 | Ando et al. | |
| 2008/0200663 A1 | 8/2008 | Yee et al. | |
| 2008/0216185 A1 | 9/2008 | Chesnut | |

(Continued)

FOREIGN PATENT DOCUMENTS

| GB | 2338237 A | 12/1999 |
|---|---|---|
| WO | 98/37186 A1 | 8/1998 |

(Continued)

OTHER PUBLICATIONS

Office Action from related European Patent Application No. 10803004.0, dated Feb. 5, 2014, 3 pgs.
First Office Action and Search Report from related Chinese Patent Application No. 201180029160.3, dated Jan. 6, 2014, 13 pgs.
Office Action from related U.S. Appl. No. 13/641,050, dated Oct. 25, 2013, 19 pgs.
Office Action from related Chinese Patent Application No. 201180029129.X, dated Dec. 4, 2013, 13 pgs.
Office Action from related Chinese Patent Application No. 201180045842.3, dated Dec. 4, 2013, 11 pgs.

(Continued)

*Primary Examiner* — Jennifer Dunston
(74) *Attorney, Agent, or Firm* — Polsinelli PC

(57) ABSTRACT

The present invention provides methods and kits for editing specific chromosomal sequences in cells. In particular, targeting endonucleases and single-stranded nucleic acids are used to edit the chromosomal sequence.

3 Claims, 22 Drawing Sheets
(3 of 22 Drawing Sheet(s) Filed in Color)

(56) References Cited

U.S. PATENT DOCUMENTS

| | | |
|---|---|---|
| 2008/0305519 A1 | 12/2008 | Lin et al. |
| 2009/0068109 A1 | 3/2009 | Das et al. |
| 2009/0117617 A1 | 5/2009 | Holmes et al. |
| 2009/0131270 A1 | 5/2009 | Taylor et al. |
| 2009/0227029 A1 | 9/2009 | Radman et al. |
| 2010/0009352 A1 | 1/2010 | Gough et al. |
| 2010/0047805 A1 | 2/2010 | Wang |
| 2012/0192298 A1 | 7/2012 | Weinstein et al. |
| 2013/0059362 A1 | 3/2013 | Fetter et al. |
| 2013/0059388 A1 | 3/2013 | Malkov et al. |
| 2013/0065310 A1 | 3/2013 | Davis et al. |

FOREIGN PATENT DOCUMENTS

| | | |
|---|---|---|
| WO | 98/53057 A1 | 11/1998 |
| WO | 00/27878 A1 | 5/2000 |
| WO | 01/88197 A2 | 11/2001 |
| WO | 02/077227 A2 | 10/2002 |
| WO | 2005/014791 A2 | 2/2005 |
| WO | 2007/014275 | 2/2007 |
| WO | 2009/042186 A2 | 4/2009 |
| WO | 2009/054985 A1 | 4/2009 |
| WO | 2009/131632 A1 | 10/2009 |
| WO | 2010/021692 A1 | 2/2010 |
| WO | 2011/011767 | 1/2011 |
| WO | 2011/130343 | 10/2011 |
| WO | 2011/130345 | 10/2011 |
| WO | 2011/130346 | 10/2011 |
| WO | 2012/012738 | 1/2012 |

OTHER PUBLICATIONS

Hu et al., "Generation of a stable mammalian cell line for simultaneous expression of multiple genes by using 2A peptide-based lentiviral vector," Biotechnol Lett, 2009, pp. 353-359, vol. 31.

Kessels et al., "Specificity and affinity motifs for Grb2 SH2-ligand interactions," PNAS, 2002, pp. 8524-8529, vol. 99, No. 13.

Li et al., "Protein biosensors based on the principle of fluorescence resonance energy transfer for monitoring cellular dynamics," Biotechnol Lett, 2006, pp. 1971-1982, vol. 28.

Accession No. NM_005573, Nov. 12, 2012.

Accession No. NM_145899, Nov. 18, 2012.

Argast, G. et al., "I-Ppol and I-Crel Homing Site Sequence Degeneracy Determined by Random Mutagenesis and Sequential in Vitro Enrichment," J. Mol. Biol., Jul. 17, 1998, pp. 345-353, vol. 280, No. 3.

Ashworth, J. et al., "Computational redesign of endonuclease DNA binding and cleavage specificity," Nature, Jun. 1, 2006, pp. 656-659, vol. 441.

Beerli, R. et al., "Engineering polydactyl zinc-finger transcription factors," Nat. Biotechnol., Feb. 2002, pp. 135-141, vol. 20.

Belfort, M. et al., "Homing endonucleases: keeping the house in order," Nucleic Acids Res., 1997, pp. 3379-3388, vol. 25, No. 17.

Beumer, et al. "Efficient gene targeting in *Drosophilia* by direct embryo injection with zinc-finger nucleases," PNAS, Dec. 16, 2008, p. 19821-19826, vol. 105, No. 50.

Bibikova et al., "Stimulation of Homologous Recombination through Targeted Cleavage by Chimeric Nucleases," Molecular and Cellular Biology, 2001, pp. 289-297, vol. 21, No. 1.

Bitinaite, J. et al., "FokI dimerization is required for DNA cleavage," PNAS, Sep. 1998, pp. 10570-10575, vol. 95.

Chandrasegaran, S. et al., "Chimeric Restriction Enzymes: What Is Next?," Biol. Chem., Jul./Aug. 1999, pp. 841-848, vol. 380.

Chevalier, B. et al., "Design, Activity, and Structure of a Highly Specific Artificial Endonuclease," Molec. Cell, Oct. 2002, pp. 895-905, vol. 10.

Choo, Y. et al., "Advances in zinc finger engineering," Curr. Opin. Struct. Biol., 2000, pp. 411-416, vol. 1interna0.

De Felipe, P. et al., "E unum pluribus: multiple proteins from a self-processing polyprotein," Trends in Biotechnology, Feb. 2006, pp. 68-75, vol. 24, No. 2.

Doyon, Y. et al., "Heritable Targeted Gene Disruption in Zebrafish Using Designed Zinc Finger Nucleases," Nat. Biotechnol., Jun. 2008, pp. 702-708, vol. 26, No. 6.

Dujon, B. et al., "Mobile introns: definition of terms and recommended nomenclature," Gene, 1989, pp. 115-118, No. 82.

Epinat, J.-C. et al., "A novel engineered meganuclease induces homogolous recombination in yeast and mammalian cells," Nucleic Acids Res., 2003, pp. 2952-2962, vol. 31, No. 11.

Genbank Accession No. NM_001101, Feb. 28, 2010.

Genbank Accession No. NM_006082, Apr. 5, 2010.

Geurts, A. et al., "Knockout Rats via Embryo Microinjection of Zinc-Finger Nucleases," Science, Jul. 24, 2009, p. 433, vol. 325.

Geurts, A. et al., "Knockout Rats via Embryo Microinjection of Zinc-Finger Nucleases," Supporting Online Material, www.sciencemag.org/cgi/content/full/325/5939/433/DC1; 2009; 15 pages.

Gimble, F. et al., "Substrate Recognition and Induced DNA Distortion by the PI-Scel Endonuclease, an Enzyme Generated by Protein Splicing," J. Mol. Biol., Oct. 25, 1996, pp. 163-180, vol. 263, No. 2.

Goldberg, A. et al., "Distinct Factors Control Histone Variant H3.3 Localization at Specific Genomic Regions," Cell, Mar. 5, 2010, pp. 678-691, vol. 140.

Gribskov, M. et al., "Sigma factors from *E. coli*, B. subtilis, phage SP01, and phage T4 are homogolous proteins," Nucl. Acids Res., 1986, pp. 6745-6763, vol. 14, No. 16.

International Search Report and Written Opinion dated Nov. 15, 2010 for related International Patent Application No. PCT/US2010/043167; 7 pages.

International Search Report and Written Opinion dated Aug. 17, 2011 for related International Patent Application No. PCT/US2011/32216; 13 pages.

International Search Report and Written Opinion dated Aug. 19, 2011 for related International Patent Application No. PCT/US2011/32218; 11 pages.

International Search Report and Written Opinion dated Jul. 20, 2011 for related International Patent Application No. PCT/US2011/32214; 10 pages.

International Search Report and Written Opinion dated Dec. 9, 2011 for related International Patent Application No. PCT/US2011/045037; 8 pages.

Isalan, M. et al., "A rapid, generally applicable method to engineer zinc fingers illustrated by targeting the HIV-1 promoter," Nat. Biotechnol., Jul. 2001, pp. 656-660, vol. 19, No. 7.

Jasin, M., "Genetic manipulation of genomes with rare-cutting endonucleases," Trends Genet., Jun. 1996, pp. 224-228, vol. 12, No. 6.

Jiang, X. et al., "Grb2 Regulates Internalization of EGF Receptors through Clathrin-coated Pits," Molecular Biology of the Cell, Mar. 2003, pp. 858-870, vol. 14.

Jiang, X. et al., "Coordinated Traffic of Grb2 and Ras during Epidermal Growth Factor Receptor Endocytosis Visualized in Living Cells," Molecular Biology of the Cell, May 2002, pp. 1522-1535, vol. 13.

Kim, Y-G. et al., "Chimeric restriction endonuclease," PNAS, Feb. 1994, pp. 883-887, vol. 91.

Kim, Y-G. et al., "Insertion and Deletion Mutants of FokI Restriction Endonuclease," J. Biol. Chem., Dec. 16, 1994, pp. 31978-31982, vol. 269, No. 50.

Lebrec, H. et al., "Influenza virus host resistance models in mice and rats: utilization for immune function assessment and immunotoxicology," Toxicology, Jul. 1, 1994, pp. 179-188, vol. 91, No. 2.

Li, L. et al., "Functional domains in Fok I restriction endonuclease," PNAS, May 1992, pp. 4275-4279, vol. 89.

Li, L., et al., "Alteration of the cleavage distance of Fok I restriction endonuclease by insertion mutagenesis," PNAS, Apr. 1993, pp. 2764-2768, vol. 90.

Liu, J. et al., "Sequence Conversion by Single Strand Oligonucleotide Donors via Non-homologous End Joining in Mammalian Cells," J. Biol. Chem, Jul. 23, 2010, pp. 23198-23207, vol. 285, No. 30.

(56) References Cited

OTHER PUBLICATIONS

Lombardo, A. et al., "Gene editing in human stem cells using zinc finger nucleases and integrase-defective lentiviral vector delivery," Nat. Biotechnology, Nov. 2007, pp. 1298-1306, vol. 25, No. 11.
Makkerh, J. et al., "Comparative mutagenesis of nuclear localization signals reveals the importance of neutral and acidic amino acids," Current Biology, 1996, pp. 1025-1027, vol. 6, No. 8.
Mandell, J. et al., "Zinc Finger Tools: custom DNA-binding domains for transcription factors and nucleases," Nuc. Acid Res., 2006, pp. W516-W523, vol. 34.
Mashimo et al., "Generation of Knockout Rats with X-Linked Severe Combined Immunodeficiency (X-SCID) Using Zinc-Finger Nucleases," Plos One, 2010, p. e8870, vol. 5, No. 1.
Moehle, E. et al., "Targeted gene addition into a specified location in the human genome using designed zinc finger nucleases," PNAS, Feb. 27, 2007, pp. 3055-3060, vol. 104, No. 9.
Pabo, C. et al., "Design and Selection of Novel CYS2HIS2 Zinc Finger Proteins," Annu. Rev. Biochem., 2001, pp. 313-340, vol. 70.
Paques, F. et al., "Meganucleases and DNA Double-Stranded Break-Induced Recombination: Perspectives for Gene Therapy," Current Gene Therapy, 2007, pp. 49-66, vol. 7.
Perez, E. et al., "Establishment of HIV-1 resistance in CD4+ T cells by genome editing using zinc-finger nuclease," Nature Biotech., Jul. 2008, pp. 808-816, vol. 26, No. 7.
Perler, F. et al., "Protein splicing elements: inteins and exteins—a definition of terms and recommended nomenclature," Nucleic Acids Res., 1994, pp. 1125-1127, vol. 22, No. 7.
Porteus, M. et al., "Gene targeting using zinc finger nucleases," Nature Biotech., Aug. 2005, pp. 967-973, vol. 23, No. 8.
Remy, S. et al., "Zinc-finger nucleases: a powerful tool for genetic engineering of animals," Transgenic Res., Published online Sep. 26, 2009, pp. 363-371, vol. 19.
Roberts, R. et al., "REBASE: restriction enzymes and methyltransferases," Nucleic Acid Res., 2003, pp. 418-420, vol. 31, No. 1.
Office Action from related European Patent Application No. 11769489.3, dated Jul. 2, 2014, 3 pgs.
Office Action from related U.S. Appl. No. 13/641,050, dated Jun. 27, 2014, 20 pgs.
Office Action from related U.S. Appl. No. 13/641,023, dated Jul. 8, 2014, 22 pgs.
Second Office Action from related Chinese Patent Application No. 201180029129.X, dated Aug. 12, 2014, 15 pgs.
Second Office Action from related Chinese Patent Application No. 201180029160.3, dated Aug. 12, 2014, 17 pgs.
Aoki et al., "Visualization of small GTPase activity with fluorescence resonance energy transfer-based biosensors", Nature Protocols, 2009, pp. 1623-1631, vol. 4, No. 11.
Batzer et al., "Hierarchy of Binding Sites for Grb2 and Shc on the Epidermal Growth Factor Receptor", Molecular and Cellular Biology, 1994, pp. 5192-5201, vol. 14, No. 8.
*Homo sapiens* arrestin domain containing containing 2, transcript variant 1, downloaded Jun. 26, 2014 GenBank Accession No. NM_015683, publicly available Jan. 26, 2014.
*Homo sapiens* POTE ankyrin domain family, member E (POTEE), transcript variant X1, downloaded Jun. 26, 2014 GenBank Accession No. XM_006712538, publicly available Feb. 3, 2014.
Choidas et al., "The suitability and application of a GFP-actin fusion protein for long-term imaging of the organization and dynamics of the cytoskeleton in mammalian cells", European Journal of Cell Biology, 1998, pp. 81-90, vol. 77.
Hahn et al., "Live-cell fluorescent biosensors for activated signaling proteins", Current Opinion in Cell Biology, 2002, pp. 167-172, vol. 14.
Hotulainen et al., "Stress fibers are generated by two distinct actin assembly mechanisms in motile cells", The Journal of Cell Biology, 2006, pp. 383-394, vol. 173, No. 3.
Huh et al., "Global analysis of protein localization in budding yeast", Nature, 2003, pp. 686-691, vol. 425.

Kiyokawa et al., "Fluorescence (Forster) resonance energy transfer imaging of oncogene activity in living cells", Cancer Sci., 2006, pp. 8-15, vol. 97, No. 1.
Miyawaki "Visualization of the Spatial and Temporal Dynamics of Intracellular Signaling", Developemental Cell, 2003, p. 295-305, vol. 4.
Valdez et al., "Green Fluorescent Protein Tag for Studies of Drug-Induced Translocation of Nucleolar Protein RH-II/Gu", BioTechniques, 1998, pp. 1032-1036, vol. 24, No. 6.
Durai et al., "Zinc finger nucleases: custom-designed molecular scissors for genome engineering of plant and mammalian cells", Nucleic Acids Research, 2005, pp. 5978-5990, vol. 33, No. 18.
GenBank: U20114.1, "Cricetulus griseus beta-actin (ACTB) gene, complete cds", NCBI Accession, priority to Apr. 6, 1995; 2 pgs.
Second Office Action from related Chinese Patent Application No. 201180045842.3, dated Oct. 27, 2014; 9 pgs.
Office Action from related U.S. Appl. No. 13/641,023, dated Nov. 18, 2014; 18 pgs.
Office Action from related U.S. Appl. No. 13/641,036, dated Dec. 11, 2014; 16 pgs.
Sander, J. et al., "Zinc Finger Targeter (ZiFiT): an engineered zinc finger/ target site design tool," Nucleic Acid Res., 2007, pp. W599-W605, vol. 35.
Santiago, Y. et al., "Targeted gene knockout in mammalian cells by using engineered zinc-finger nucleases," PNAS, Apr. 15, 2008, pp. 5809-5814, vol. 105, No. 15.
Segal, D. et al., "Custom DNA-binding proteins come of age: polydactyl zinc-finger proteins," Curr. Opin. Biotechnol., 2001, pp. 632-637, vol. 12.
Sera, T. et al., "Rational Design of Artificial Zinc-Finger Proteins Using a Nondegenerate Recognition Code Table," Biochemistry, 2002, pp. 7074-7081, vol. 41.
Smith, T. et al., "Comparison of Biosequences," Advances in Applied Mathematics, 1981, pp. 482-489, vol. 2.
Ting, A. et al., "Genetically encoded fluorescent reporters of protein tyrosine kinase activities in living cells," PNAS, Dec. 18, 2001, pp. 15003-15008, vol. 98, No. 26.
UniProtKB/Swiss-Prot accession No. P04626, Aug. 13, 1987.
Urnov, F. et al., "Highly efficient endogenous human gene correction using designed zinc-finger nucleases," Nature, Jun. 2, 2005, pp. 646-651, vol. 435.
Urnov, F. et al., "Genome editing with engineered zinc finger nucleases," Nature Rev. Genet., Sep. 2010, pp. 636-646, vol. 11, No. 9.
Wu, J. et al., "Custom-designed zinc finger nucleases: What is next?" Cell Mol. Life Science, Nov. 2007, pp. 2933-2944, vol. 64, No. 22.
Yaoi, T. et al., "Src Homology 2 Domain-based High Throughput Assays for Profiling Downstream Molecules in Receptor Tyrosine Kinase Pathways," Molecular & Cellular Proteomics, 2006, pp. 959-968, vol. 5.
Zhang, Y. et al., "Solution Structure of the E200K Variant of Human Prion Protein," J. Biol. Chem., Oct. 27, 2000, pp. 33850-33860, vol. 275, No. 43.
Zou, J. et al., "Gene targeting of a disease-related gene in human induced pluripotent stem and embryonic stem cells," Cell Stem Cell, Jul. 2, 2009, pp. 97-100, vol. 5, No. 1 (Author Manuscript).
Carroll, "Progress and prospects: Zinc-finger nucleases as gene therapy agents", Gene Therapy, 2008, pp. 1463-1468, vol. 15, No. 22.
Chung et al., "Regulatory Elements Mediating Transcription from the *Drosophila melanogaster* Actin 5C Proximal Promoter", Molecular and Cellular Biology, 1990, pp. 206-216, vol. 10, No. 1.
Hockemeyer et al., "Efficient targeting of expressed and silent genes in human ESCs and iPSCs using zinc-finger nucleases", Nature Biotechnology, 2009, pp. 851-857, vol. 27, No. 9.
Ng et al., "Regulation of the human β-actin promoter by upstream and intron domains", Nucleic Acids Research, 1989, pp. 601-615, vol. 17, No. 2.
Office Action from related U.S. Appl. No. 13/641,023, dated Apr. 20, 2015; 12 pgs.
Office Action from related Japanese Patent Application No. 2013-505077, dated May 26, 2015; 9 pgs.

(56) References Cited

OTHER PUBLICATIONS

Office Action from related Japanese Patent Application No. 2013-505078, dated May 26, 2015; 7 pgs.
Office Action from related U.S. Appl. No. 13/641,050, dated Jun. 4, 2015; 10 pgs.
Office Action from related U.S. Appl. No. 13/641,050 dated Jan. 29, 2015; 14 pgs.
Third Office Action from related Chinese Patent Application No. 201180029129.X, dated Feb. 16, 2015; 11 pgs.
Third Office Action from related Chinese Patent Application No. 201180029160.3, dated Feb. 16, 2015; 14 pgs.
Office Action from related U.S. Appl. No. 13/641,036, dated Mar. 31, 2015; 12 pgs.
Supplementary European Search Report from related European Application No. 11810474.4, dated Mar. 16, 2015; 3 pgs.
Office Action from related European Application No. 11810474.4, dated Nov. 6, 2015; 3 pgs.
Third Office Action from related Chinese Patent Application No. 201180045842.3, dated Jul. 13, 2015; 9 pgs.
Office Action from related U.S. Appl. No. 13/641,023, dated Aug. 19, 2015; 12 pgs.
Office Action from related U.S. Appl. No. 13/641,023, dated Dec. 7, 2015; 13 pgs.
Office Action from related U.S. Appl. No. 13/641,050, dated Dec. 17, 2015; 15 pgs.
Office Action from related U.S. Appl. No. 13/641,036, dated Aug. 26, 2015; 16 pgs.
Office Action from related U.S. Appl. No. 13/641,036, dated Dec. 18, 2015; 24 pgs.
Office Action from related Chinese Patent Application No. 201180029160.3, dated Sep. 2, 2015; 13 pgs.
Office Action from related Japanese Patent Application No. 2013-520886, dated Nov. 10, 2015; 4 pgs.
Alberts et al., "Molecular Biology of THE CELL", Fifth Edition, Chapter 16: The Cytoskeleton, New York: Garland Science, 2008, pp. 965-1052.
Kim et al., "Targeted genome editing in human cells with zinc finger nucleases constructed via modular assembly", Genome Research, 2009, pp. 1279-1288, vol. 19.
Mummidi et al., "The Human CC Chemokine Receptor 5 (CCR5) Gene", The Journal of Biological Chemistry, 1997, pp. 30662-30671, vol. 272, No. 49.
Stauffer et al., "Compartmentalized IgE Receptor-mediated Signal Transduction in Living Cells", The Journal of Cell Biology, 1997, pp. 1447-1454, vol. 139, No. 6.
Chen et al., "High-frequency genome editing using ssDNA oligo-nucleotides with zinc-finger nucleases", Nature Methods, 2011, pp. 753-757, vol. 8, No. 9, along with 26 pages of supplemental material.
DeKelver et al., "Functional genomics, proteomics, and regulatory DNA analysis in isogenic settings using zinc finger nuclease-driven transgenesis into a safe harbor locus in the human genome", Genome Research, 2010, pp. 1133-1142, vol. 20, along with 16 pages of supplementary information.
UniProtKB—Accession No. O75364 (PITX3_HUMAN), PITX3—Pituitary homeobox 3—*Homo sapiens* (Human)—PITX3 gene & protein, downloaded Nov. 11, 2015, http://www.uniprot.org/uniprot/O75364; 3 pgs.
UniProtKB—Accession No. Q01860 (P05F1_HUMAN), POU5F1—POU domain, class 5, transcription factor 1—*Homo sapiens* (Human)—POU5F, downloaded Oct. 23, 2015, http://www.uniprot.org/uniprot/Q01860; 18 pgs.
Written Opinion from related Singapore Application No. 2013002944, dated Nov. 20, 2015; 6 pgs.
Radecke et al., "Targeted Chromosomal Gene Modification in Human Cells by Single-Stranded Oligodeoxynucleotides in the Presence of a DNA Double-Strand Break," Molecular Therapy, 2006, pp. 798-808, vol. 14, No. 6.

\* cited by examiner

RSK2 wild type genomic sequence (top) (SEQ ID NO:1)

5'-GGATATGAAGTAAAAGAAGAGATATTGGAGTTGGCTCCTACTCTGTTTGCAAGAGATGTATACATAAAGCTACAAACAT
GGAGTTTGCAGTGAAGGTAAATTTTTTTATTTAAAATGCAATTCATA-3'
   ZFN Right Binding Site                                ZFN Left Binding Site Oligo carrying mutations (bottom) (SEQ ID NO:2)

BamHI Site
5'-
GGATATGAAGTAAAAGAAGAGATATTGGAGTTGG_TCCTACTCTGTTGTTAAGAGATGTATACATAAAGCAACAAACAT
GGAGTTTGCAGTGAAGGTAAATTTTTTTATTTAAAATGCAATTCATA-3'
Cys to Val

FIG. 1

AAVS1 wild type genomic sequence (SEQ ID NO:3)

5'-CTGGTTCTGGGTACTTTTATCTGTCCCTCCACCCCACAGTGGGGCCACTAGGGACACAGGATTGGTGACAGAAAAGCCCCATCCTTAGGCCTCTCCTT-3'
                                                        ZFN Left Binding Site          ZFN Right Binding Site Sense Strand Oligo (SEQ ID NO:4)

5'-CTGGTTCTGGGTACTTTTATCTGTCCCTCCACCCCACAGTGGGGC[AAGCTTGAAT]ACTAGGGACACAGGATTGGTGACAGAAAAGCCCCATCCTTAGGCCTCTCCTT-3'
                                                    HindIII Site Anti-Sense Strand Oligo (SEQ ID NO:5)

3'-GACCAAGACCCATGAAAATAGACAGGGAGGTGGGGTGTCACCCCG[TTCGAACTTA]TGATCCCTGTGTCCTAACCACTGTCTTTTCGGGGTAGGAATCCGGAGAGGAA-5'

FIG. 4

SENSE READ tggccact TTTCATTTGGGCAGCTCCCCTTACCTCTCT
AGTCTGTGCTAGTTCTTTCCAGGCCCTGTCATGGCATTTCCAGGGTCCGAG
AGCTCAGCTAGTCTTCTCTGCCAACCCGGCCATTGTCCACTTCAGGACA
GCATGTTTGCTGCCCAGGATCCTGTGTCCCGAGGTGGACACTTATA
TTCCCAGGGCCGGTTAATGTGGCTCTGGTACTTTTATCTGTCCCTC
CAGCCCACAGTGGGTCAATTCCCCTGCAGGACAACGCCACACACCAGTTA
GCCTTTAAGCCTGCCCAGAAGACTCCCGCCACCGGCGGGTCTGAAT tggattg
SEQ. ID NO. 29

FIG. 18

Sense Read ggctgattTTCTGTACAGTCTCGAGGTTAAACGTCGACTCTCCCGGGAGAAAG
ACTGGAGTTGCAGATCACGAGGGAAGAGAGGGGAAGGATTCCCAGGCCAGGGC
GGTCCCTCAGAAGCTAGGGACAGGATTGGTCTAACCCCACATCCTTAGCCT
CTCCTTCTAGTCTCTGATATTGGGTGTAACCCACCTCTGTTAAGCAGATTC
CTTATCTGGTTGACACCCCATTTCTGGCAGTCTCTGTCTCCTTGCCAGAACTCT
AA

SEQ. ID NO. 30

FIG. 19

SEQUENCE LISTING

<160> NUMBER OF SEQ ID NOS: 30

<210> SEQ ID NO 1
<211> LENGTH: 125
<212> TYPE: DNA
<213> ORGANISM: Homo sapiens

<400> SEQUENCE: 1
ggatatgaag taaagaaga tattggagtt ggctcctact ctgtttgcaa gagatgtata      60
cataaagcta caaacatgga gtttgcagtg aaggtaaatt tttttatttt aaaatgcaat    120
tcata                                                                125

<210> SEQ ID NO 2
<211> LENGTH: 125
<212> TYPE: DNA
<213> ORGANISM: Artificial Sequence
<220> FEATURE:
<223> OTHER INFORMATION: SYNTHESIZED

<400> SEQUENCE: 2
ggatatgaag taaaagaaga tattggagtt ggatcctact ctgttgttaa gagatgtata    60
cataaagcaa caaacatgga atttgcagtg aaggtaaatt ttttttattt aaaatgcaat   120
tcata                                                              125

<210> SEQ ID NO 3
<211> LENGTH: 98
<212> TYPE: DNA
<213> ORGANISM: Homo sapiens

<400> SEQUENCE: 3
ctggttctgg gtacttttat ctgtcccctc caccccacag tggggccact agggacagga    60
ttggtgacag aaaagcccca tccttaggcc tcctcctt                            98

<210> SEQ ID NO 4
<211> LENGTH: 108
<212> TYPE: DNA
<213> ORGANISM: Artificial Sequence
<220> FEATURE:
<223> OTHER INFORMATION: SYNTHESIZED

<400> SEQUENCE: 4
ctggttctgg gtacttttat ctgtcccctc caccccacag tggggcaagc ttgaagtact    60
agggacagga ttggtgacag aaaagcccca tccttaggcc tcctcctt                108

<210> SEQ ID NO 5
<211> LENGTH: 108
<212> TYPE: DNA
<213> ORGANISM: Artificial Sequence
<220> FEATURE:
<223> OTHER INFORMATION: SYNTHESIZED

<400> SEQUENCE: 5
aaggaggagg cctaaggatg gggcttttct gtcaccaatc ctgtccctag tacttcaagc    60
ttgccccact gtggggtgga ggggacagat aaaagtaccc agaaccag                108

<210> SEQ ID NO 6
<211> LENGTH: 15
<212> TYPE: DNA
<213> ORGANISM: Homo sapiens

<400> SEQUENCE: 6
gtatacataa agcta                                                    15

<210> SEQ ID NO 7
<211> LENGTH: 19
<212> TYPE: DNA
<213> ORGANISM: Homo sapiens

<400> SEQUENCE: 7
ggagtttgca gtgaaggta                                                19

<210> SEQ ID NO 8
<211> LENGTH: 12

```
<212> TYPE: DNA
<213> ORGANISM: Homo sapiens

<400> SEQUENCE: 8
accccacagt gg                                                              12

<210> SEQ ID NO 9
<211> LENGTH: 12
<212> TYPE: DNA
<213> ORGANISM: Homo sapiens

<400> SEQUENCE: 9
tagggacagg at                                                              12

<210> SEQ ID NO 10
<211> LENGTH: 106
<212> TYPE: DNA
<213> ORGANISM: Artificial Sequence
<220> FEATURE:
<223> OTHER INFORMATION: SYNTHESIZED

<400> SEQUENCE: 10
ggctctggtt ctgggtactt ttatctgtcc cctccacccc acagtggggc aagcttcact          60
agggacagga ttggtgacag aaaagcccca tccttaggcc tcctcc                        106

<210> SEQ ID NO 11
<211> LENGTH: 86
<212> TYPE: DNA
<213> ORGANISM: Artificial Sequence
<220> FEATURE:
<223> OTHER INFORMATION: SYNTHESIZED

<400> SEQUENCE: 11
ctgggtactt ttatctgtcc cctccacccc acagtggggc aagcttcact agggacagga          60
ttggtgacag aaaagcccca tcctta                                               86

<210> SEQ ID NO 12
<211> LENGTH: 66
<212> TYPE: DNA
<213> ORGANISM: Artificial Sequence
<220> FEATURE:
<223> OTHER INFORMATION: SYNTHESIZED

<400> SEQUENCE: 12
ttatctgtcc cctccacccc acagtggggc aagcttcact agggacagga ttggtgacag          60
aaaagc                                                                     66

<210> SEQ ID NO 13
<211> LENGTH: 56
<212> TYPE: DNA
<213> ORGANISM: Artificial Sequence
<220> FEATURE:
<223> OTHER INFORMATION: SYNTHESIZED

<400> SEQUENCE: 13
tgtcccctcc accccacagt ggggcaagct tcactaggga caggattggt gacaga              56

<210> SEQ ID NO 14
<211> LENGTH: 46
<212> TYPE: DNA
<213> ORGANISM: Artificial Sequence
<220> FEATURE:
<223> OTHER INFORMATION: SYNTHESIZED
```

<400> SEQUENCE: 14
cctccacccc acagtggggc aagcttcact agggacagga ttggtg                46

<210> SEQ ID NO 15
<211> LENGTH: 36
<212> TYPE: DNA
<213> ORGANISM: Artificial Sequence
<220> FEATURE:
<223> OTHER INFORMATION: SYNTHESIZED

<400> SEQUENCE: 15
accccacagt ggggcaagct tcactaggga caggat                           36

<210> SEQ ID NO 16
<211> LENGTH: 106
<212> TYPE: DNA
<213> ORGANISM: Artificial Sequence
<220> FEATURE:
<223> OTHER INFORMATION: SYNTHESIZED

<400> SEQUENCE: 16
ggaggaggcc taaggatggg gcttttctgt caccaatcct gtccctagtg aagcttgccc    60
cactgtgggg tggaggggac agataaaagt acccagaacc agagcc                106

<210> SEQ ID NO 17
<211> LENGTH: 86
<212> TYPE: DNA
<213> ORGANISM: Artificial Sequence
<220> FEATURE:
<223> OTHER INFORMATION: SYNTHESIZED

<400> SEQUENCE: 17
taaggatggg gcttttctgt caccaatcct gtccctagtg aagcttgccc cactgtgggg    60
tggaggggac agataaaagt acccag                                      86

<210> SEQ ID NO 18
<211> LENGTH: 66
<212> TYPE: DNA
<213> ORGANISM: Artificial Sequence
<220> FEATURE:
<223> OTHER INFORMATION: SYNTHESIZED

<400> SEQUENCE: 18
gcttttctgt caccaatcct gtccctagtg aagcttgccc cactgtgggg tggaggggac    60
agataa                                                            66

<210> SEQ ID NO 19
<211> LENGTH: 56
<212> TYPE: DNA
<213> ORGANISM: Artificial Sequence
<220> FEATURE:
<223> OTHER INFORMATION: SYNTHESIZED

<400> SEQUENCE: 19
tctgtcacca atcctgtccc tagtgaagct tgccccactg tggggtggag gggaca        56

<210> SEQ ID NO 20
<211> LENGTH: 36
<212> TYPE: DNA
<213> ORGANISM: Artificial Sequence
<220> FEATURE:
<223> OTHER INFORMATION: SYNTHESIZED

<400> SEQUENCE: 20

```
atcctgtccc tagtgaagct tgccccactg tggggt                              36
```

<210> SEQ ID NO 21
<211> LENGTH: 100
<212> TYPE: DNA
<213> ORGANISM: Artificial Sequence
<220> FEATURE:
<223> OTHER INFORMATION: SYNTHESIZED

<400> SEQUENCE: 21

```
ataagcaggt gaagttagaa catccacaaa agtataaaat tgactcttct gtcctgtgtg    60
ctagggacag gattggtgac agaaaagccc catccttagg                         100
```

<210> SEQ ID NO 22
<211> LENGTH: 100
<212> TYPE: DNA
<213> ORGANISM: Artificial Sequence
<220> FEATURE:
<223> OTHER INFORMATION: SYNTHESIZED

<400> SEQUENCE: 22

```
aggagaattt gtaggcttca agagaccatg ttgtaacagg tgggtgataa caggctttaa    60
ctagggacag gattggtgac agaaaagccc catccttagg                         100
```

<210> SEQ ID NO 23
<211> LENGTH: 100
<212> TYPE: DNA
<213> ORGANISM: Artificial Sequence
<220> FEATURE:
<223> OTHER INFORMATION: SYNTHESIZED

<400> SEQUENCE: 23

```
tacccaaaga agcttcttcc actctgataa aagaaaggaa aaataggcaa agccacagac    60
ctagggacag gattggtgac agaaaagccc catccttagg                         100
```

<210> SEQ ID NO 24
<211> LENGTH: 110
<212> TYPE: DNA
<213> ORGANISM: Artificial Sequence
<220> FEATURE:
<223> OTHER INFORMATION: SYNTHESIZED

<400> SEQUENCE: 24

```
atccacaaaa gtataaaatt gactcttctg tcctgtgtgt aacttcgtat agcatacatt    60
atacgaagtt atctagggac aggattggtg acagaaaagc ccatcccta              110
```

<210> SEQ ID NO 25
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 25

```
ttcgggtcac ctctcactcc                                                20
```

<210> SEQ ID NO 26
<211> LENGTH: 22
<212> TYPE: DNA
<213> ORGANISM: Artificial Sequence
<220> FEATURE:
<223> OTHER INFORMATION: SYNTHESIZED

```
<400> SEQUENCE: 26
acctcgagac cggtggatcc ga                                            22

<210> SEQ ID NO 27
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 27
gcggtctgaa ttcggatcca ccg                                           23

<210> SEQ ID NO 28
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 28
ggctccatcg taagcaaacc                                               20

<210> SEQ ID NO 29
<211> LENGTH: 363
<212> TYPE: DNA
<213> ORGANISM: Artificial Sequence
<220> FEATURE:
<223> OTHER INFORMATION: SYNTHESIZED

<400> SEQUENCE: 29
tctcactcct ttcatttggg cagctcccct accccccttaa cctctctagt ctgtgctagc   60
tcttccagcc ccctgtcatg gcatcttcca ggggtccgag agctcagcta gtcttcttcc  120
tccaacccgg gccctatgt ccacttcagg acagcatgtt tgctgcctcc agggatcctg   180
tgtccccgag ctgggaccac cttatattcc cagggccggt taatgtggct ctggttctgg  240
gtacttttat ctgtcccctc cacccacag tgggtcaatt ccctgcagg acaacgccca   300 cacaccaggt tagcctttaa gcctgcccag aagactcccg cccaccgcgg tctgaattcg  360
gat                                                                363

<210> SEQ ID NO 30
<211> LENGTH: 310
<212> TYPE: DNA
<213> ORGANISM: Artificial Sequence
<220> FEATURE:
<223> OTHER INFORMATION: SYNTHESIZED

<400> SEQUENCE: 30
gcggtctgaa ttcggatcca ccggtctcga ggtttaaacg tcgactctcc cgggagaaag   60
actggagttg cagatcacga gggaagaggg ggaagggatt ctcccaggcc cagggcggtc  120
cctcagaagc tagggacagg attggtgaca gaaaagcccc atccttaggc ctcctccttc  180
ctagtctcct gatattgggt ctaaccccca cctcctgtta aggcagattc cttatctggt  240
gacacacccc catttcctgg agccatctct ctccttgcca gaacctctaa ggtttgctta  300
cgatggagcc                                                          310
```

GENOME EDITING USING TARGETING ENDONUCLEASES AND SINGLE-STRANDED NUCLEIC ACIDS

CROSS REFERENCE TO RELATED APPLICATIONS

This application is a U.S. national stage application of PCT International Application No. PCT/US2011/045037, filed Jul. 22, 2011, which claims the priority of U.S. Provisional Application No. 61/410,124, filed Nov. 4, 2010, U.S. Provisional Application No. 61/382,965, filed Sep. 15, 2010, and U.S. Provisional Application No. 61/367,022, filed Jul. 23, 2010, each of which is hereby incorporated by reference in its entirety.

FIELD OF THE INVENTION

The invention generally relates to the use of targeting endonucleases and single-stranded nucleic acids to edit specific chromosomal sequences.

BACKGROUND OF THE INVENTION

Rationale genome engineering has enormous potential across basic research, drug discovery, and cell-based medicines. Many existing methods for targeted gene knock-out, mutagenesis, or integration rely on homologous recombination. The low rate of spontaneous recombination in many cells, as well as the scale of screening effort and time required to isolate the targeted event, however, have hindered progress in this field. Thus, there exists a need for a technology that can rapidly achieve targeted genome editing with high speed, efficiency, and accuracy.

SUMMARY OF THE INVENTION

Among the various aspects of the present disclosure is the provision of a method for editing at least one endogenous chromosomal sequence in a cell. The method comprises introducing into the cell (i) at least one targeting endonuclease or nucleic acid encoding a targeting endonuclease, wherein the targeting endonuclease is able to introduce a double-stranded break at a targeted cleavage site in the chromosomal sequence, and (ii) at least one single-stranded nucleic acid comprising a first portion having substantial sequence identity to the chromosomal sequence on at least one side of the targeted cleavage site. The method further comprises maintaining the cell under conditions such that the double-stranded break introduced by the targeting endonuclease is repaired by a homology-directed process such that the chromosomal sequence is exchanged with the sequence of the single-stranded nucleic acid, thereby editing the chromosomal sequence.

A further aspect provides a kit for editing a chromosomal sequence in a cell. The kit comprises (a) at least one targeting endonuclease or nucleic acid encoding a targeting endonuclease, wherein the targeting endonuclease is able to introduce a double-stranded break at a targeted cleavage site in the chromosomal sequence, and (b) at least one single-stranded nucleic acid comprising a first portion having substantial sequence identity to the chromosomal sequence on at least one side of the targeted cleavage site.

Other aspects and features of the disclosure are described more thoroughly below.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 presents the design of the oligonucleotide used to modify the RSK2 kinase locus. The RSK2 kinase wild-type genomic sequence is presented at the top, with the ZFN binding sites indicated. The sequence of the oligonucleotide harboring specific mutations is presented at the bottom.

FIG. 4 diagrams the design of the oligonucleotides used to modify the AAVS1 locus. The AAVS1 wild-type genomic sequence is presented at the top, with the ZFN binding sites indicated. The sequences of sense and anti-sense oligonucleotides comprising a site are shown below.

FIG. 18 presents the 5' junction sequence (SEQ ID NO: 29) and sequence analysis confirming the integration of the donor sequence at the 5' junction. Sequence in highlighted green represents the primers used for PCR amplification (lower case was not from sequencing results), sequence in black letters represents mouse Rosa26 plasmid sequence not in the oligonucleotide donor; sequence in blue letters represents mouse Rosa26 plasmid sequence in oligonucleotide donor; sequence in red letters represents AAVS1 sequence in oligonucleotide donor; sequence in pink letters represents AAVS1 sequence not in oligonucleotide donor.

FIG. 19 presents the 3' junction sequence (SEQ ID NO: 30) and sequence analysis confirming the integration of the donor sequence at the 3' junction. Sequence in highlighted green represents the primers used for PCR amplification (lower case was not from sequencing results), sequence in black letters represents mouse Rosa26 plasmid sequence not in the oligonucleotide donor; sequence in blue letters represents mouse Rosa26 plasmid sequence in oligonucleotide donor; sequence in red letters represents AAVS1 sequence in oligonucleotide donor; sequence in pink letters represents AAVS1 sequence not in oligonucleotide donor.

DETAILED DESCRIPTION OF THE INVENTION

Figure 2:
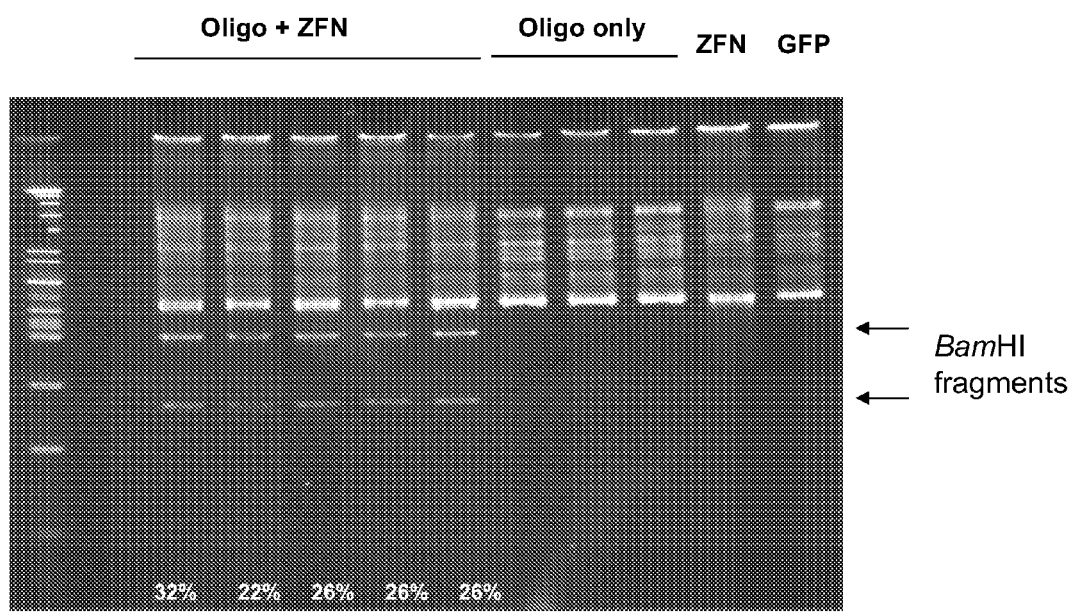
FIG. 2 documents the integration of the BamHI site into the RSK2 kinase locus. Pools of cells were digested with BamHI and the fragments were resolved by gel electrophoresis.

The present disclosure provides methods for editing endogenous chromosomal sequences using targeting endonucleases and single-stranded nucleic acids. In particular, the targeting endonuclease is able to introduce a double-stranded break at targeted site in the chromosomal sequence, and the single-stranded nucleic acid comprises a region having substantial sequence identity to the chromosomal sequence on at least one side of the targeted cleavage site. The double-stranded break introduced by the targeting endonuclease is repaired by a homology-directed repair process using the single-stranded nucleic acid such that the chromosomal sequence is exchanged with the sequence of the single-stranded nucleic acid, thereby editing the chromosomal sequence. The edited chromosomal sequence may comprise an insertion of at least one nucleotide, a deletion of at least one nucleotide, a substitution of at least one nucleotide, or combinations thereof. Also provided herein are kits comprising the appropriate reagents for editing chromosomal sequences using the methods disclosed herein.

(I) Methods for Editing Chromosomal Sequences

One aspect of the present disclosure provides a method for editing at least one endogenous chromosomal sequence in a cell. The method comprises introducing into the cell (a) at least one targeting endonuclease or nucleic acid encoding a targeting endonuclease, the targeting endonuclease being able to introduce a double-stranded break at a targeted cleavage site in the chromosomal sequence, and (b) at least one single-stranded nucleic acid comprising a sequence having substantially sequence identity to the chromosomal sequence on at least one side of the targeted cleavage site. The method further comprises maintaining the cell under conditions such that the double-stranded break introduced by the targeting endonuclease is repaired by a homology-directed repair process such that the chromosomal sequence is exchanged with the sequence of at least one of the single-stranded nucleic acids, thereby editing the chromosomal sequence. Components of the method are detailed below.

(a) Targeting Endonuclease

The method comprises introducing into the cell at least one targeting endonuclease or nucleic acid encoding a targeting endonuclease. A targeting endonuclease is an entity that recognizes and binds a specific double-stranded chromosomal DNA sequence and introduces a double-stranded break at a targeted cleavage site in the chromosomal sequence. The targeting endonuclease may be a naturally-occurring protein or an engineered protein. Alternatively, the targeting endonuclease may contain no protein (e.g., an artificial targeted DNA double strand break inducing agent).

The type of targeting endonuclease can and will vary. In some embodiments, the targeting endonuclease may be a zinc finger nuclease. In other embodiments, the targeting endonuclease may be a meganuclease or homing endonuclease. In still other embodiments, the targeting endonuclease may be a transcription activator-like effector (TALE)-nuclease. In further embodiments, the targeting endonuclease may be a site-specific nuclease. In still other embodiments, the targeting endonuclease may be an artificial targeted DNA double strand break inducing agent.

(i) Zinc Finger Nuclease

In one embodiment, the targeting endonuclease introduced into the cell may be a zinc finger nuclease (ZFN). Typically, a zinc finger nuclease comprises a DNA binding domain (i.e., zinc finger) and a cleavage domain (i.e., nuclease), both of which are described below.

Zinc finger binding domain. Zinc finger binding domains may be engineered to recognize and bind to any nucleic acid sequence of choice. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:411-416; Zhang et al. (2000) J. Biol. Chem. 275(43): 33850-33860; Doyon et al. (2008) Nat. Biotechnol. 26:702-708; and Santiago et al. (2008) Proc. Natl. Acad. Sci. USA 105:5809-5814. An engineered zinc finger binding domain may have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm of described in U.S. Pat. No. 6,453,242 may be used to design a zinc finger binding domain to target a preselected sequence. Alternative methods, such as rational design using a nondegenerate recognition code table may also be used to design a zinc finger binding domain to target a specific sequence (Sera et al. (2002) Biochemistry 41:7074-7081). Publically available web-based tools for identifying potential target sites in DNA sequences and designing zinc finger binding domains may be found at www.zincfingertools.org and bindr.gdcb.iastate.edu/ZiFiT/, respectively (Mandell et al. (2006) Nuc. Acid Res. 34:W516-W523; Sander et al. (2007) Nuc. Acid Res. 35:W599-W605).

A zinc finger binding domain may be designed to recognize and bind a DNA sequence ranging from about 3 nucleotides to about 21 nucleotides in length, or preferably from about 9 to about 18 nucleotides in length. In general, the zinc finger binding domains of the zinc finger nucleases disclosed herein comprise at least three zinc finger recognition regions (i.e., zinc fingers). In one embodiment, the zinc finger binding domain may comprise four zinc finger recognition regions. In another embodiment, the zinc finger binding domain may comprise five zinc finger recognition regions. In still another embodiment, the zinc finger binding domain may comprise six zinc finger recognition regions. A zinc finger binding domain may be designed to bind to any suitable target DNA sequence. See for example, U.S. Pat. Nos. 6,607,882; 6,534,261 and 6,453,242, the disclosures of which are incorporated by reference herein in their entireties.

Exemplary methods of selecting a zinc finger recognition region may include phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237, each of which is incorporated by reference herein in its entirety. In addition, enhancement of binding specificity for zinc finger binding domains has been described, for example, in WO 02/077227.

Zinc finger binding domains and methods for design and construction of fusion proteins (and polynucleotides encoding same) are known to those of skill in the art and are described in detail in U.S. Patent Application Publication Nos. 20050064474 and 20060188987, each incorporated by reference herein in its entirety. Zinc finger recognition regions and/or multi-fingered zinc finger proteins may be linked together using suitable linker sequences, including for example, linkers of five or more amino acids in length. See, U.S. Pat. Nos. 6,479,626; 6,903,185; and 7,153,949, the disclosures of which are incorporated by reference herein in their entireties, for non-limiting examples of linker sequences of six or more amino acids in length. The zinc finger binding domain described herein may include a combination of suitable linkers between the individual zinc fingers of the protein.

In some embodiments, the zinc finger nuclease may further comprise a nuclear localization signal or sequence (NLS). A NLS is an amino acid sequence which facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027.

Cleavage Domain. A zinc finger nuclease also includes a cleavage domain. The cleavage domain portion of the zinc finger nuclease may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res. 25:3379-3388 or www.neb.com. Additional enzymes that cleave DNA are known (e.g., S1 Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) may be used as a source of cleavage domains.

A cleavage domain also may be derived from an enzyme or portion thereof, as described above, that requires dimerization for cleavage activity. Two zinc finger nucleases may be required for cleavage, as each nuclease comprises a monomer of the active enzyme dimer. Alternatively, a single zinc finger nuclease may comprise both monomers to create an active enzyme dimer. As used herein, an "active enzyme dimer" is an enzyme dimer capable of cleaving a nucleic acid molecule. The two cleavage monomers may be derived from the same endonuclease (or functional fragments thereof), or each monomer may be derived from a different endonuclease (or functional fragments thereof).

When two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites may be separated by about 5 to about 18 nucleotides. For instance, the near edges may be separated by about 5, 6, 7, 8, 9, 10, 11, 12, 13, 14, 15, 16, 17 or 18 nucleotides. It will however be understood that any integral number of nucleotides or nucleotide pairs may intervene between two recognition sites (e.g., from about 2 to about 50 nucleotide pairs or more). The near edges of the recognition sites of the zinc finger nucleases, such as for example those described in detail herein, may be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982. Thus, a zinc finger nuclease may comprise the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31:418-420.

An exemplary Type IIS restriction enzyme, whose cleavage domain is separable from the binding domain, is FokI. This particular enzyme is active as a dimer (Bitinaite et al. (1998) Proc. Natl. Acad. Sci. USA 95: 10, 570-10, 575). Accordingly, for the purposes of the present disclosure, the portion of the FokI enzyme used in a zinc finger nuclease is considered a cleavage monomer. Thus, for targeted double-stranded cleavage using a FokI cleavage domain, two zinc finger nucleases, each comprising a FokI cleavage monomer, may be used to reconstitute an active enzyme dimer. Alternatively, a single polypeptide molecule containing a zinc finger binding domain and two FokI cleavage monomers may also be used.

In certain embodiments, the cleavage domain may comprise one or more engineered cleavage monomers that minimize or prevent homodimerization, as described, for example, in U.S. Patent Publication Nos. 20050064474, 20060188987, and 20080131962, each of which is incorporated by reference herein in its entirety. By way of non-limiting example, amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Exemplary engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499.

Thus, in one embodiment, a mutation at amino acid position 490 replaces Glu (E) with Lys (K); a mutation at amino acid residue 538 replaces Iso (I) with Lys (K); a mutation at amino acid residue 486 replaces Gln (Q) with Glu (E); and a mutation at position 499 replaces Iso (I) with Lys (K). Specifically, the engineered cleavage monomers may be prepared by mutating positions 490 from E to K and 538 from I to K in one cleavage monomer to produce an engineered cleavage monomer designated "E490K:I538K" and by mutating positions 486 from Q to E and 499 from I to L in another cleavage monomer to produce an engineered cleavage monomer designated "Q486E:I499L." The above described engineered cleavage monomers are obligate heterodimer mutants in which aberrant cleavage is minimized or abolished. Engineered cleavage monomers may be prepared using a suitable method, for example, by site-directed mutagenesis of wild-type cleavage monomers (FokI) as described in U.S. Patent Publication No. 20050064474.

(ii) Other Targeting Endonucleases

In another embodiment, the targeting endonuclease may be a meganuclease. Meganucleases are endodeoxyribonucleases characterized by a large recognition site, i.e., the recognition site generally ranges from about 12 base pairs to about 40 base pairs. As a consequence of this requirement, the recognition site generally occurs only once in any given genome. Among meganucleases, the LAGLIDADG family of homing endonucleases has become a valuable tool for the study of genomes and genome engineering. Meganucleases can be targeted to specific chromosomal sequence by modifying their recognition sequence using techniques well known to those skilled in the art.

In a further embodiment, the targeting endonuclease may be a transcription activator-like effector (TALE) nuclease. TALEs are transcription factors from the plant pathogen Xanthomonas that can be readily engineered to bind new DNA targets. TALEs or truncated versions thereof may be linked to the catalytic domain of endonucleases such as FokI to create targeting endonuclease called TALE nucleases or TALENs.

In still another embodiment, the targeting endonuclease may be a site-specific nuclease. In particular, the site-specific nuclease may be a "rare-cutter" endonuclease whose recognition sequence occurs rarely in a genome. Preferably, the recognition sequence of the site-specific nuclease occurs only once in a genome.

In yet another embodiment, the targeting endonuclease may be an artificial targeted DNA double strand break inducing agent (also called an artificial restriction DNA cutter). For example, the artificial targeted DNA double strand break inducing agent may comprise a metal/chelator complex that cleaves DNA and at least one oligonucleotide that is complementary to the targeted cleavage site. The artificial targeted DNA double strand break inducing agent, therefore, does not contain any protein, The metal of the metal/chelator complex may be cerium, cadmium, cobalt, chromium, copper, iron, magnesium, manganese, zinc, and the like. The chelator of the metal/chelator complex may be EDTA, EGTA, BAPTA, and so forth. In a preferred embodiment, the metal/chelator complex may be Ce(IV)/EGTA. In another preferred embodiment, the artificial targeted DNA double strand break inducing agent may comprise a complex of Ce(IV)/EGTA and two strands of pseudo-complementary peptide nucleic acids (PNAs) (Katada et al., Current Gene Therapy, 2011, 11(1):38-45).

(iii) Nucleic Acids Encoding the Targeting Endonuclease

In some embodiments, the targeting endonuclease may be introduced into the cell as a nucleic acid, wherein the cell then expresses and produces the targeting endonuclease. The nucleic acid encoding the targeting endonuclease may be DNA or RNA. The RNA may be messenger RNA, and the mRNA may be 5' capped, polyadenylated, or both. In general, the nucleic acid encoding the targeting endonuclease will be operably linked to a promoter control region. The control region may be constitutive or inducible. The nucleic acid encoding the targeting endonuclease (and its linked control region) may be introduced into the cell as a vector such as a plasmid or the like. Alternatively, the nucleic acid encoding the targeting endonuclease (and its linked control region) may be introduced into the cell as a linear molecule.

(b) Single-Stranded Nucleic Acids (i) General Properties

The method further comprises introducing into the cell at least one single-stranded nucleic acid comprising a region having substantial sequence identity to the chromosomal sequence on at least one side of the targeted cleavage site. In some embodiments, one single-stranded nucleic acid is introduced into the cell. In other embodiments, two single-stranded nucleic acids are introduced into the cell. In further embodiments, three or more single-stranded nucleic acids are introduced into the cell.

The phrase "substantial sequence identity" means that the oligonucleotide has at least about 75% sequence identity with the targeted chromosomal sequence. In some embodiments, the oligonucleotide may have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with the targeted chromosomal sequence. Additionally, the single-stranded nucleic acid generally has substantial sequence identity to at least about 10 nucleotides on at least one side of the targeted cleavage site. In some embodiment, the single-stranded nucleic acid may have substantial sequence identity to about 15 nucleotides, about 20 nucleotides, about 25 nucleotides, about 30 nucleotides, about 40 nucleotides, about 50 nucleotides, about 100 nucleotides, or more than 100 nucleotides on at least one side of the targeted cleavage site.

The length of the single-stranded nucleic acids that are introduced into the cell can and will vary. For example, the single-stranded nucleic acids may range from about 20 nucleotides in length up to about 200,000 nucleotides in length. In various embodiments, the single-stranded nucleic acid may range from about 20 nucleotides to about 100 nucleotides in length, from about 100 nucleotides to about 1000 nucleotides in length, from about 1000 nucleotides to about 10,000 nucleotides in length, from about 10,000 nucleotides to about 100,000 nucleotides in length, or from about 100,000 nucleotides to about 200,000 nucleotides in length.

In some embodiments, the single-stranded nucleic acids may be linear. In other embodiments, the single-stranded nucleic acids may be circular (e.g., prepared by phage methods known to those of skill in the art). The single-stranded nucleic acid may be sense or anti-sense relative to the chromosomal sequence of interest.

The composition of the single-stranded nucleic acids can and will vary. The nucleotides of the nucleic acid may be deoxyribonucleotides, ribonucleotides, or combinations thereof. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos. The nucleotides of the single-stranded nucleic acids may be linked by phosphodiester, phosphothioate, phosphoramidite, phosphorodiamidate bonds, or combinations thereof.

In preferred embodiments, the single-stranded nucleic acid comprises deoxyribonucleotides.

(ii) Preferred Single-Stranded Nucleic Acids

In one embodiment, the single-stranded nucleic acid may comprise a first region with substantial sequence identity to the chromosomal sequence at the upstream side of the targeted cleavage site and a second region with substantial sequence identity to the chromosomal sequence at the downstream side of the targeted cleavage site (e.g., see FIG. 1 and FIG. 4). In various iterations of this embodiment, the single-stranded nucleic acid may further comprise a change of at least one nucleotide relative to the chromosomal sequence. For example, the single-stranded nucleic acid will generally comprise a substitution of at least one nucleotide, a deletion of at least one nucleotide, an insertion of at least one nucleotide, or combinations thereof. In various iterations, the single-stranded nucleic acid may comprise one, two, three, four, five, or more nucleotide changes. As a consequence of these nucleotide changes, the edited chromosomal sequence may comprise an altered sequence or a small mutation such that a modified gene product is produced, no gene product is produced, etc.

In an alternate embodiment, the single-stranded nucleic acid may comprise an exogenous sequence that is flanked by the first and second regions that have substantial sequence identity to either side of the targeted cleavage site (as detailed above.) Consequently, the edited chromosomal sequence may comprise an integrated exogenous nucleic acid sequence. As used herein, the term "exogenous" refers to any sequence that is not normally located at that chromosomal location. For example, the exogenous sequence may be a "gene" from another organism, an additional copy of a "gene" from the same organism, an artificial sequence, a sequence encoding a reporter molecule, and so forth.

Figure 12:
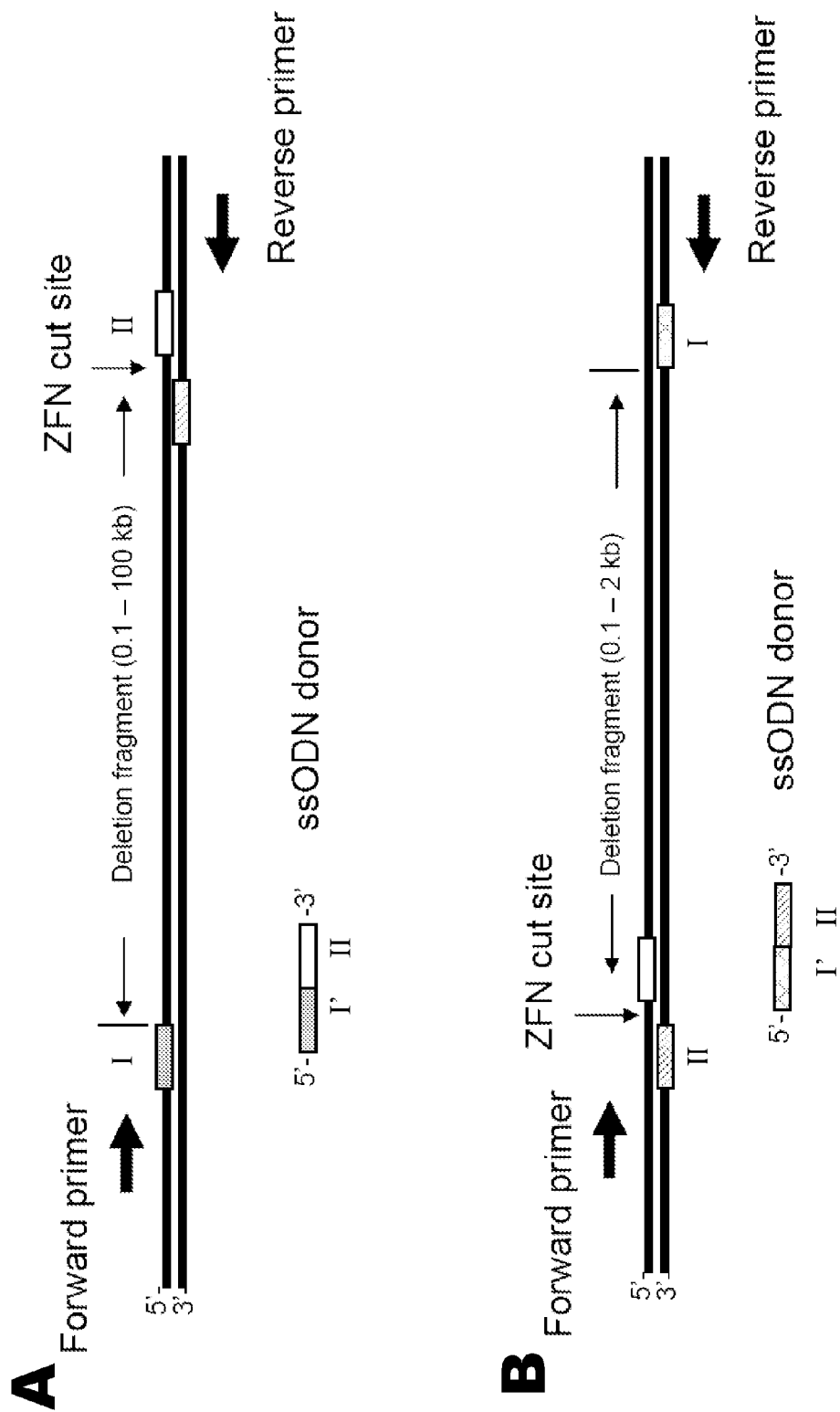
FIG. 12 illustrates the targeted deletion of 0.1-100 kb genomic DNA at a specific locus with single-stranded DNA oligonucleotides (ssODN) and ZFNs. Panel A illustrates a deletion that is 5' to the ZFN cleavage site. Panel B illustrates a deletion that is 3' to the ZFN cleavage site. The distant deletion endpoint region in the chromosomal sequence designated as I, and the ZFN binding site near the targeted cleavage site is designated as II. The ssODN donor comprises a region (designated as I') that has sequence identity to the distant deletion endpoint region and a region (designated as II) that has sequence identity to the ZFN binding site near the targeted cleavage site.

In another embodiment, the single-stranded nucleic acid may comprise a first region with substantial sequence identity to the chromosomal sequence on one side of the targeted cleavage site and a second region with substantial sequence identity to a chromosomal sequence that is distal to the targeted cleavage site (see FIG. 12). The distal chromosomal sequence may be upstream or downstream of the targeted cleavage site; and the distal chromosomal sequence may be located from about 20 base pairs to about 1,000,000 base pairs away from the targeted cleavage site. For example, the distal chromosomal sequence may be about 0.1, 0.3, 1, 3, 10, 30, 100, 300, or 1,000 kilobase pairs (upstream or downstream) of the targeted cleavage site. As a consequence, the edited chromosomal sequence may comprise a deletion of up to about 1,000,000 base pairs. In one iteration of this embodiment, the single-stranded nucleic acid may comprise a first region with substantial sequence identity to the downstream side of the targeted cleavage site and a second region with substantial sequence identity to a distal chromosomal sequence that is located upstream of the targeted cleavage site, wherein the edited chromosomal may comprise an upstream (or 5') deletion relative to the targeted cleavage site. In another iteration of this embodiment, the single-stranded nucleic acid may comprise a first region with substantial sequence identity to the upstream side of the targeted cleavage site and a second region with substantial sequence identity to a distal chromosomal sequence that is located downstream of the targeted cleavage site, wherein the edited chromosomal may comprise a downstream (or 3') deletion relative to the targeted cleavage site.

In yet another embodiment, the single-stranded nucleic acid may comprise an exogenous sequence that is flanked by a first region with substantial sequence identity to the chromosomal sequence on one side of the targeted cleavage site and a second region with substantial sequence identity to a chromosomal sequence that is distal to the targeted cleavage site (as detailed above). In this embodiment, the edited chromosomal sequence may comprise a deletion, as well as integration of the exogenous sequence at the targeted cleavage site (see FIG. 16). The identity of the exogenous sequence can and will vary. For example, the exogenous sequence may be a "gene" from another organism, an additional copy of a "gene" from the same organism, a reporter molecule, and so forth.

(c) Optional Donor Polynucleotide

In certain embodiments, the method further comprises introducing at least one donor polynucleotide into the cell. The donor polynucleotide comprises a sequence for integration into the chromosomal sequence at the targeted cleavage site, wherein the sequence for integration is flanked by a first sequence and a second sequence, each of which has substantial sequence identity to a portion of a single-stranded nucleic acid. Thus, the donor polynucleotide is introduced along with a first single-stranded nucleic acid and a second single-stranded nucleic acid (and at least one targeting endonuclease). The first single-stranded nucleic acid comprises a first portion having substantial sequence identity to the upstream side of the targeted cleavage site, and a second portion with substantial sequence identity to the first sequence in the donor polynucleotide. The second single-stranded nucleic acid comprises a first portion having substantial sequence identity to the downstream side of the targeted cleavage site and a second portion with substantial sequence identity to the second sequence in the donor polynucleotide.

The donor polynucleotide may comprise deoxyribonucleotides, ribonucleotides, modified nucleotides, nucleotide analogs, and the like. Moreover, the donor polynucleotide may be circular or linear. Typically, the donor polynucleotide will be DNA. For example, the donor polynucleotide may be a DNA plasmid, a bacterial artificial chromosome (BAC), a yeast artificial chromosome (YAC), a viral vector, and so forth. The donor polynucleotide may further comprise an origin of replication, a selection marker, a multiple cloning site, and so forth. The size of the donor polynucleotide can and will vary. For example, the donor nucleotide may range from about 1 kilobase (kb) to about 200 kb. In one embodiment, the donor polynucleotide may comprise about 100 kb of exonic and intronic sequences of a human DNA sequence encoding a protein of interest.

(d) Cells

The method comprises introducing the targeting endonuclease molecules(s) and nucleic acid(s) described above into a cell. A variety of cells are suitable for use in the method. In general, the cell will be a eukaryotic cell or a single cell eukaryotic organism. In some instances, the cell may be a cultured cell, a primary cell, or an immortal cell. Suitable cells include fungi or yeast, such as *Pichia*, *Saccharomyces*, or *Schizosaccharomyces*; insect cells, such as SF9 cells from *Spodoptera frugiperda* or S2 cells from *Drosophila melanogaster*; and animal cells, such as mouse, rat, hamster, non-human primate, or human cells. Exemplary cells are mammalian. The mammalian cells may be primary cells. In general, any primary cell that is sensitive to double strand breaks may be used. The cells may be of a variety of cell types, e.g., fibroblast, myoblast, T or B cell, macrophage, epithelial cell, and so forth.

When mammalian cell lines are used, the cell line may be any established cell line or a primary cell line that is not yet described. The cell line may be adherent or non-adherent, or the cell line may be grown under conditions that encourage adherent, non-adherent or organotypic growth using standard techniques known to individuals skilled in the art. Non-limiting examples of suitable mammalian cell lines include Chinese hamster ovary (CHO) cells, monkey kidney CVI line transformed by SV40 (COS7), human embryonic kidney line 293, baby hamster kidney cells (BHK), mouse sertoli cells (TM4), monkey kidney cells (CVI-76), African green monkey kidney cells (VERO), human cervical carcinoma cells (HeLa), canine kidney cells (MDCK), buffalo rat liver cells (BRL 3A), human lung cells (W138), human liver cells (Hep G2), mouse mammary tumor cells (MMT), rat hepatoma cells (HTC), HIH/3T3 cells, human U2-OS osteosarcoma cells, human A549 cells, human K562 cells, human HEK293 cells, human HEK293T cells, human HCT116 cells, human MCF-7 cells, and TRI cells. For an extensive list of mammalian cell lines, those of ordinary skill in the art may refer to the American Type Culture Collection catalog (ATCC®, Manassas, Va.).

In still other embodiments, the cell may be a stem cell. Suitable stem cells include without limit embryonic stem cells, ES-like stem cells, fetal stem cells, adult stem cells, pluripotent stem cells, induced pluripotent stem cells, multipotent stem cells, oligopotent stem cells, and unipotent stem cells.

In further embodiments, the cell may be a one-cell embryo. The embryo may be a vertebrate or an invertebrate. Suitable vertebrates include mammals, birds, reptiles, amphibians, and fish. Examples of suitable mammals include without limit rodents, companion animals, livestock, and non-primates. Non-limiting examples of rodents include mice, rats, hamsters, gerbils, and guinea pigs. Suitable companion animals include but are not limited to cats, dogs, rabbits, hedgehogs, and ferrets. Non-limiting examples of livestock include horses, goats, sheep, swine, cattle, llamas, and alpacas. Suitable non-primates include but are not limited to capuchin monkeys, chimpanzees, lemurs, macaques, marmosets, tamarins, spider monkeys, squirrel monkeys, and vervet monkeys. Non-limiting examples of birds include chickens, turkeys, ducks, and geese. Alternatively, the animal may be an invertebrate such as an insect, a nematode, and the like. Non-limiting examples of insects include Drosophila and mosquitoes.

(e) Delivery to the Cell

The targeting endonuclease molecules(s) and nucleic acid(s) described above may be introduced into the cell by a variety of means. Suitable delivery means include microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In one embodiment, the targeting endonuclease molecule(s) and nucleic acid(s) may be introduced into a cell by nucleofection. In another embodiment, the targeting endonuclease molecule(s) and nucleic acid(s) may be introduced into the cell (e.g., a one-cell embryo) by microinjection. The targeting endonuclease molecule(s) and nucleic acid(s) may be microinjected into the nucleus or the cytoplasm of the cell.

In embodiments in which more than one targeting endonuclease molecule and more than one single-stranded nucleic are introduced into a cell, the molecules may be introduced simultaneously or sequentially. For example, targeting endonuclease molecules, each specific for a targeted cleavage site, as well as the corresponding single-stranded nucleic acid(s), may be introduced at the same time. Alternatively, each targeting endonuclease molecule, as well as the corresponding single-stranded nucleic acid(s), may be introduced sequentially. The optional donor polynucleotides may be introduced similarly.

The ratio of the targeting endonuclease molecule(s) to the single-stranded nucleic acid(s) can and will vary. In general, the ratio of targeting endonuclease molecule(s) to nucleic acid(s) may range from about 1:10 to about 10:1. In various embodiments, the ratio of the targeting endonuclease molecule(s) to nucleic acid(s) may be about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1. In one embodiment, the ratio may be about 1:1.

(f) Culturing the Cell

The method further comprises maintaining the cell under appropriate conditions such that the double-stranded break introduced by the targeting endonuclease may be repaired by a homology-directed process using the single-stranded nucleic acid(s) such that the chromosomal sequence is edited. In embodiments in which nucleic acid(s) encoding the targeting endonuclease is introduced into the cell, the method comprises maintaining the cell under appropriate conditions such that the cell expresses the targeting endonuclease.

In general, the cell will be maintained under conditions appropriate for cell. Suitable cell culture conditions are well known in the art and are described, for example, in Santiago et al. (2008) PNAS 105:5809-5814; Moehle et al. (2007) PNAS 104:3055-3060; Urnov et al. (2005) Nature 435:646-651; and Lombardo et al (2007) Nat. Biotechnology 25:1298-1306. Those of skill in the art appreciate that methods for culturing cells are known in the art and can and will vary depending on the cell type. Routine optimization may be used, in all cases, to determine the best techniques for a particular cell type.

In embodiments in which the cell is a one-cell embryo, the embryo may be cultured in vitro (e.g., in cell culture). Typically, the embryo is cultured at an appropriate temperature and in appropriate media with the necessary $O_2/CO_2$ ratio to allow the repair of the double-stranded break and allow development of the embryo. Suitable non-limiting examples of media include M2, M16, KSOM, BMOC, and HTF media. A skilled artisan will appreciate that culture conditions can and will vary depending on the species of embryo. Routine optimization may be used, in all cases, to determine the best culture conditions for a particular species of embryo. In some instances, the embryo also may be cultured in vivo by transferring the embryo into the uterus of a female host. Generally speaking the female host is from the same or similar species as the embryo. Preferably, the female host is pseudo-pregnant. Methods of preparing pseudo-pregnant female hosts are known in the art. Additionally, methods of transferring an embryo into a female host are known. Culturing an embryo in vivo permits the embryo to develop and may result in a live birth of an animal derived from the embryo.

During this step of the process, the targeting endonuclease (which in some case is expressed from the introduced nucleic acid encoding the targeting endonuclease) recognizes, binds, and creates a double-stranded break at the targeted cleavage site in the chromosomal sequence. The double-stranded break in the chromosomal sequence is repaired, via homologous recombination with the single-stranded nucleic acid, such that the nucleic acid sequence is exchanged with the chromosomal sequence. The nucleic acid sequence may be physically integrated or, alternatively, the nucleic acid sequence may be used as a template for repair of the break, resulting in editing of the chromosomal sequence.

The frequency of the targeted editing of the chromosomal sequence can and will vary depending upon a variety of factors. In some embodiments, the frequency of editing may be greater than about 0.01%, 0.03%, 0.1%, 0.3%, 1%, 3%, 10%, or 30%. Single cell clones comprising the edited chromosomal sequence may be isolated using techniques well known in the art. Persons skilled in the art are familiar with methods for generating cells homozygous for the edited chromosomal sequence. Stated another way, cells may be heterozygous or homozygous for the edited chromosomal sequence.

The edited chromosomal sequence may comprise one or more point mutations (i.e., wherein one nucleotide is substituted for another nucleotide), one or more deletions, and/or one or more insertions. The point mutations may be missense mutations, nonsense mutations, or silent mutations. The deletions may range from about one base pair to about 500 kilobase pairs, and the insertions may range from about one base pair to about 200 kilobase pairs.

The edited chromosomal sequence, therefore, may give rise to a modified gene product (i.e., protein or non-coding RNA). For example, in embodiments in which the edited chromosomal sequence lies within a protein coding region, the resultant protein may comprise at least one amino acid change. In other embodiments, the modified chromosomal sequence may give rise to a modified non-coding RNA, or the modified chromosomal sequence may have an altered regulatory function.

Alternatively, the edited chromosomal sequence may be inactivated such that no functional gene product is produced (or the function of a regulatory region is eliminated). For example, in embodiments in which the edited chromosomal sequence lies within a protein coding region, the point mutation(s), deletion(s), and/or insertion(s) may introduce premature stop codons, splice-site junction mutations, and/or frame shift mutation such that no functional protein is produced.

In embodiments in which the edited chromosomal sequence comprises an insertion, the inserted sequence may encode a peptide, a protein, a protein domain, a protein fragment, a protein subunit, a protein tag, and the like. Alternatively, the inserted sequence may provide a restriction endonuclease recognition side, encode a non-coding RNA, comprise a microRNA binding site, or function as a transcriptional control element.

(II) Cells Comprising at Least One Edited Chromosomal Sequence

Another aspect of the disclosure provides cells comprising at least one edited chromosomal sequence, wherein the chromosomal sequence was edited by the method described above in section (I). Suitable cells are detailed above in section (I)(d).

(III) Kits

A further aspect encompasses kits for editing chromosomal sequences in a cell. A kit comprises (a) at least one targeting endonuclease or nucleic acid encoding a targeting endonuclease, wherein the targeting endonuclease is able to introduce a double-stranded break at a targeted cleavage site in the chromosomal sequence, and (b) at least one single-stranded nucleic acid comprising a first portion having substantial sequence identity to the chromosomal sequence on at least one side of the targeted cleavage site. Thus, the kit provides means for editing a chromosomal sequence using the method detailed above in section (I).

The kit may further comprise one or more additional reagents useful for practicing the disclosed method for genome editing using targeting endonucleases and single-stranded nucleic acids. A kit generally includes a package with one or more containers holding the reagents, as one or more separate compositions or, optionally, as admixture where the compatibility of the reagents will allow. The kit may also include other material(s), which may be desirable from a user standpoint, such as a buffer(s), a diluent(s), culture medium/media, standard(s), and/or any other material useful in processing or conducting any step of the genome editing method.

The kits provided herein preferably include instructions for editing chromosomal sequences as detailed above in section (I). Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

(IV) Applications

The method of editing chromosomal sequences disclosed herein may have a variety of applications. In some embodiments, the method may be used for research purposes to introduce targeted mutations into a protein of interest such that the function of the modified protein may be examined. The method may also be used to inactivate a protein coding sequence such that no protein is produced, wherein the phenotype of the cell or organism comprising the cells may be examined. Additionally, the method may be used to modify or inactivate RNA coding regions or transcriptional control regions for research purposes. In still other embodiments, the method may be used to delete large regions of chromosomal sequence and/or integrate exogenous nucleic acid sequences.

In other embodiments, the method disclosed herein may be used for clinical or therapeutic purposes. That is, the method may be used to repair or correct disease-causing genes or chromosomal sequences. As an example, sickle-cell disease may be caused by a single nucleotide change (i.e., an A to T change in the β-globin gene results in a glutamate to valine change in the β-globin protein). Accordingly, the method of this disclosure may be used to correct the SNP in the β-globin gene in cells of an individual having sickle-cell trait or disease. Similarly, the method may be used to correct splice junction mutations, deletions, insertions, and the like in other genes or chromosomal sequences that play a role in a particular disease or disease state.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including"

and "having" are intended to be inclusive and mean that there may be additional elements other than the listed elements.

The terms "editing" or "genome editing" refer to a process by which a specific chromosomal sequence is changed. The edited chromosomal sequence may comprise an insertion of at least one nucleotide, a deletion of at least one nucleotide, and/or a substitution of at least one nucleotide. The edited modified chromosomal sequence may encode a modified gene product (e.g., a protein with an altered amino acid sequence, a non-coding RNA with an altered nucleotide sequence, etc,), provide a modified function (e.g., altered promoter function, altered enhancer function, etc.), may fail to give rise to a gene product (i.e., the sequence is not transcribed and/or no functional product is made), fail to provide a regulatory function, encode an exogenous sequence, or provide a new function (i.e., as a regulatable promoter, inducible promoter, microRNA binding site, etc.).

As used herein, the term "endogenous" refers to a chromosomal sequence that is native to the cell.

The terms "exogenous" as used herein refers to a nucleic acid sequence that is not normally located at a particular chromosomal location. An exogenous sequence may be from another organism, may be artificial, or may be a duplicate copy of a nucleic acid sequence present at another chromosomal location.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The terms "nucleic acid" and "polynucleotide" refer to a deoxyribonucleotide or ribonucleotide polymer, in linear or circular conformation. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The terms "polypeptide" and "protein" are used interchangeably to refer to a polymer of amino acid residues.

As used herein, the terms "target site" or "target sequence" refer to a nucleic acid sequence that defines a portion of a chromosomal sequence to be edited and to which a zinc finger nuclease is engineered to recognize and bind, provided sufficient conditions for binding exist.

The terms "upstream" and "downstream" refer to location in a nucleic acid sequence relative to a fixed position. Upstream refers to the region that is 5' (i.e., near the 5' end of the strand) to the position and downstream refers to the region that is 3' (i.e., near the 3' end of the strand) to the position.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations-FSwiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between regions that share a degree of sequence identity, followed by digestion with single-stranded-specific nuclease(s), and size determination of the digested fragments. Two nucleic acid, or two polypeptide sequences are substantially similar to each other when the sequences exhibit at least about 70%-75%, preferably 80%-82%, more-preferably 85%-90%, even more preferably 92%, still more preferably 95%, and most preferably 98% sequence identity over a defined length of the molecules, as determined using the methods above. As used herein, substantially similar also refers to sequences showing complete identity to a specified DNA or polypeptide sequence. DNA sequences that are substantially similar can be identified in a Southern hybridization experiment under, for example, stringent conditions, as defined for that particular system. Defining appropriate hybridization conditions is within the skill of the art. See, e.g., Sambrook et al., supra; Nucleic Acid Hybridization: A Practical Approach, editors B. D. Hames and S. J. Higgins, (1985) Oxford; Wash. D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, Nucleic Acid Hybridization: A Practical Approach, editors B. D. Hames and S. J. Higgins, (1985) Oxford; Wash. D.C.; IRL Press). Conditions for hybridization are well-known to those of skill in the art.

Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations. With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. A particular set of hybridization conditions may be selected following standard methods in the art (see, for example, Sambrook, et al., Molecular Cloning: A Laboratory Manual, Second Edition, (1989) Cold Spring Harbor, N.Y.).

EXAMPLES

The following examples are included to illustrate the invention.

Example 1

Modification of RSK2 Kinase

The following example details modification of the RSK2 kinase locus. An oligonucleotide (125 nt) was designed to incorporate three distinct mutations into the RSK2 kinase chromosomal sequence. The oligonucleotide comprised: (1) two point mutations in the ZFN binding sites to prevent subsequent non-homologous end-joining (NHEJ), (2) a TGC to GTT change to convert a Cys to a Val, and (3) a silent C to A change to create a unique BamHI site for clone screening (FIG. 1). The oligonucleotide was made using standard synthesis procedures (e.g. no chemical modifications) and was PAGE purified. A pair of zinc finger nucleases (ZFNs) was designed to target the RSK2 kinase locus. One ZFN was designed to bind the sequence 5'-GTATA-CATAAAGCTA-3' (SEQ ID NO:6; left binding site indicated in FIG. 1), and the other ZFN was designed to bind the sequence 5'-GGAGTTTGCAGTGAAGGTA-3' (SEQ ID NO:7; right binding site indicated in FIG. 1).

Human K562 cells were nucleofected with 8 μg of mRNA encoding the ZFNs and 0.3 nmol of the oligonucleotide. After two days of incubation, pools of cells were analyzed for the presence of the BamHI site. As shown in FIG. 2, cells exposed to both the oligonucleotide and the ZFNs harbored the BamHI site, whereas introduction of the oligonucleotide alone had no effect. The frequency integration ranged from about 20-30%.

Figure 3:
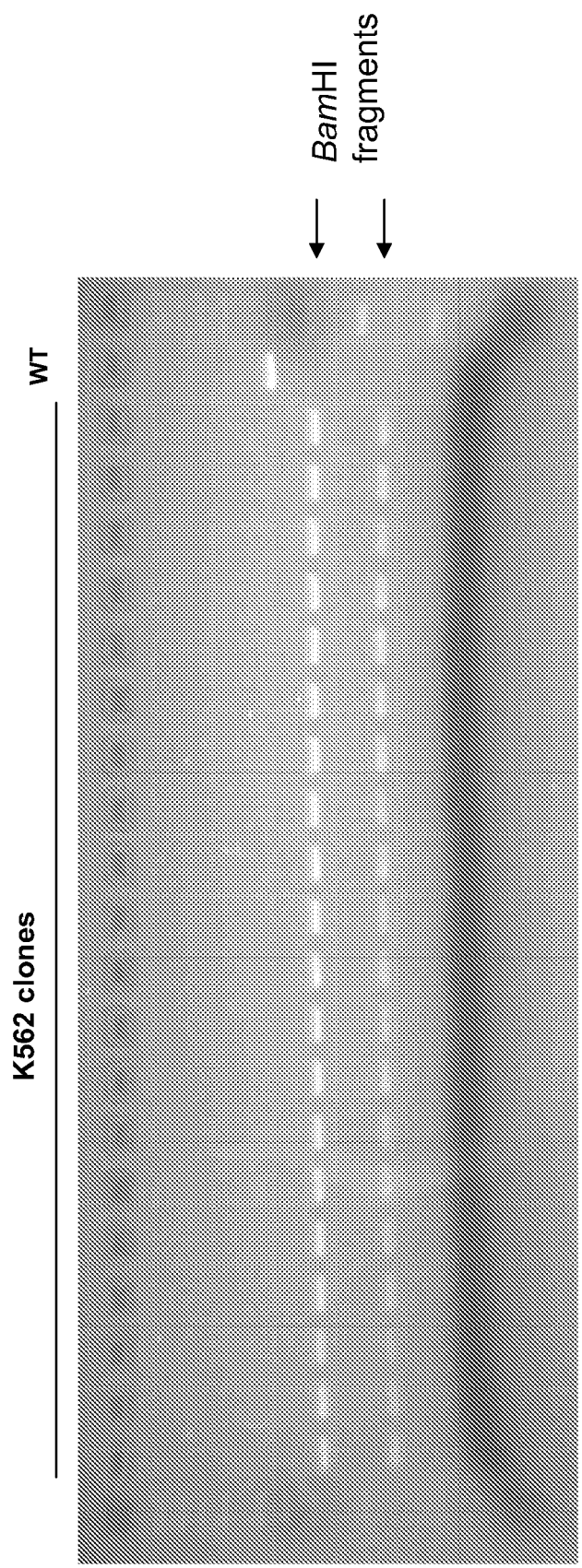
FIG. 3 depicts single isolated cell clones harboring the BamHI site at the RSK2 kinase locus. The RSK2 locus in individual clones was PCR amplified and digested with BamHI.

Single cell clones were isolated and screened using a qPCR assay to identify those harboring the BamHI site (see FIG. 3). Approximately 750 clones were screened and about 40 positive clones were identified. Positive clones were subsequently PCR amplified around the targeted chromosomal location and digested with BamHI to confirm editing of the RSK2 kinase chromosomal locus. Sequencing data revealed that the BamHI positive clones were also positive for the desired Cys to Val codon change.

Example 2

Modification of AAVS1 Locus

The following example details the use of oligonucleotides to introduce a HindIII site into the AAVS1 locus. FIG. 4 presents the wild-type sequence of the AAVS1 locus, and sequences of sense and anti-sense oligonucleotides (108 nt) comprising the HindIII site. The oligonucleotides were made using standard procedures (e.g. with no chemical modifications) and were PAGE purified.

Figure 5:
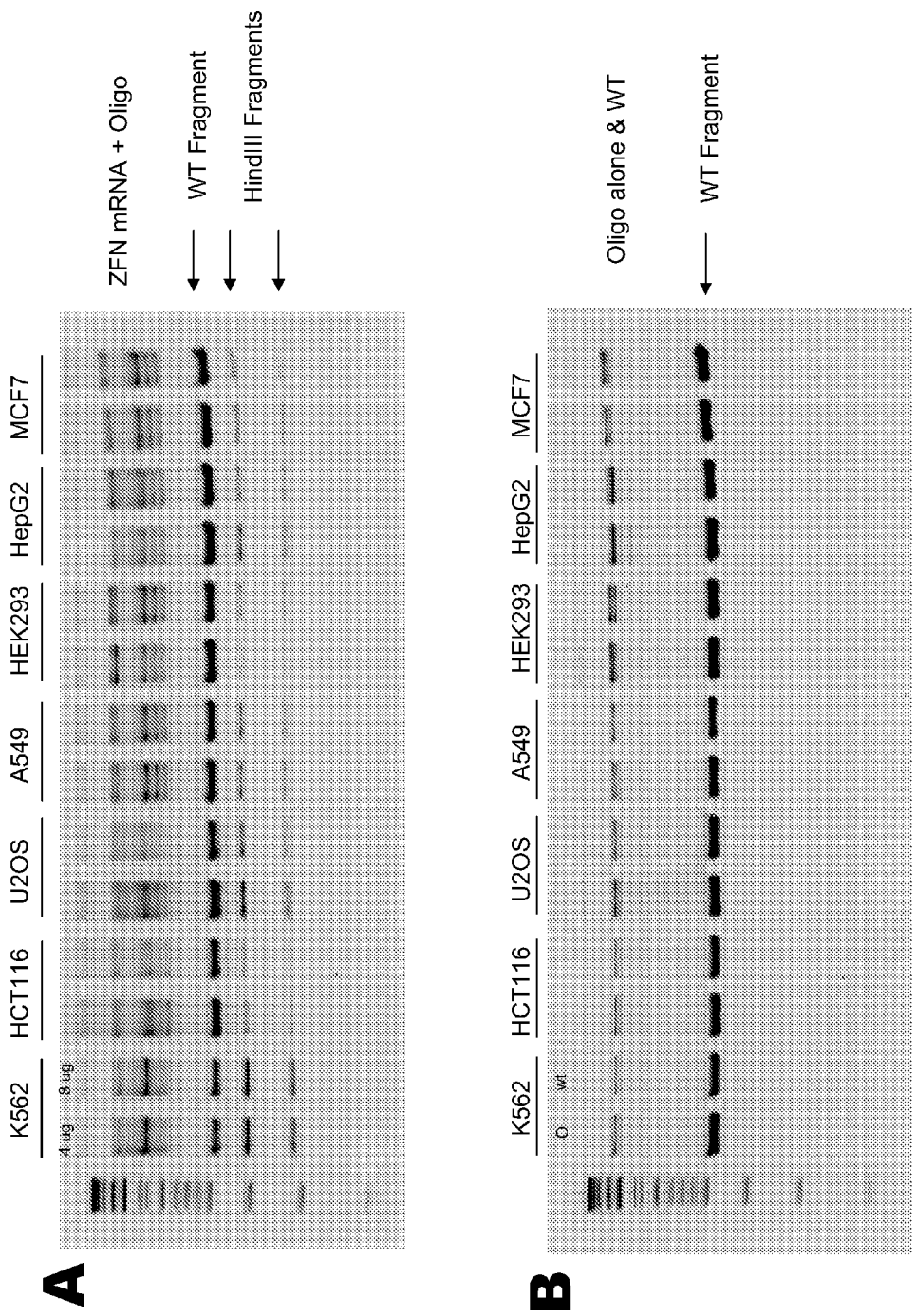
FIG. 5 illustrates integration of the HindIII site into the AAVS1 locus. Panel A depicts cells contacted with ZFN and oligonucleotide, and panel B depicts cells contacted with oligonucleotide alone. Pools of cells were digested with HindIII and the fragments were resolved by gel electrophoresis.

A pair of ZFNs was designed to target the AAVS1 locus. One ZFN was designed to bind the sequence 5'-AC-CCCACAGTGG-3' (SEQ ID NO:8; left binding site indicated in FIG. 4), and the other ZFN was designed to bind the sequence 5'-TAGGGACAGGAT-3' (SEQ ID NO:9; right binding site indicated in FIG. 4). Capped, polyadenylated mRNA encoding the ZFNs was prepared using standard procedures. The ZFN mRNA and the oligonucleotide comprising the HindIII site were nucleofected into K562, HCT116, U205, A549, HEK293, HepG2, or MSF7 cells. After a period of incubation, pools of cells were analyzed for the presence of the HindIII site. Cells exposed to both the oligonucleotide and ZFNs contained the HindIII fragments, wherein those treated with oligonucleotide alone had no HindIII fragments (FIG. 5).

Figure 6:
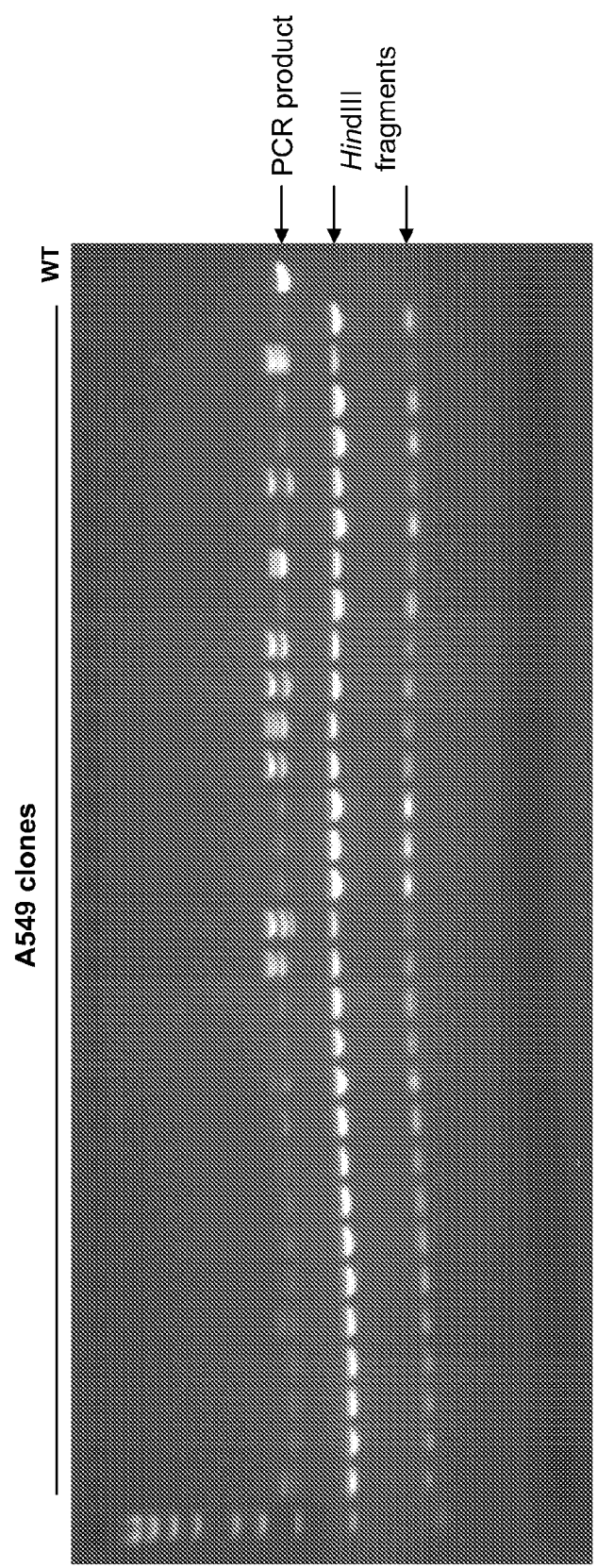
FIG. 6 depicts single isolated cell clones harboring the HindIII site at the AAVS1 locus. The AAVS1 locus in individual clones was PCR amplified and digested with HindIII.

Single cell A549 clones were isolated and screened using a qPCR assay to identify those harboring the HindIII site (FIG. 6). Approximately 933 clones were screened, with 308 identified as positive. Thus, the frequency of delivery of the HindIII site was about 33%. Positive clones were subsequently PCR amplified around the targeted chromosomal location and digested with HindIII to confirm insertion of the oligonucleotide sequence. Clones showing faint bands at the position of the parental PCR product were sequenced and confirmed to contain the HindIII site (see FIG. 6). Clones showing multiple strong bands around the position of the parental PCR product are hypothesized to contain small NHEJ-derived insertions.

Example 3

Modification of AAVS1 Locus—Length of Oligonucleotide

To determine the whether shorter oligonucleotides could be used to deliver the HindIII site to the AAVS1 locus, oligonucleotides ranging in length from 36 to 106 nt were prepared. For example, a 106 nt oligonucleotide had sequence identity to 50 nt on either side of the ZFN cleavage site (i.e., had homology arms of 50 nt), with a HindIII site (6 nt) between the homology arms. The sequences of the oligonucleotides are presented in the Table 1 below.

TABLE 1

| Oligo | DNA sequence | SEQ ID NO |
| --- | --- | --- |
| 106a | ggctctggttctgggtacttttatctgtccctccaccccacagtggggcAAGCTTcactagggacaggattggtgacagaaaagccccatccttaggcctcctcc | 10 |
| 86s | ctgggtacttttatctgtccctccaccccacagtggggcAAGCTTcactagggacaggattggtgacagaaaagccccatcctta | 11 |
| 66s | ttatctgtccctccaccccacagtggggcAAGCTTcactagggacaggattggtgacagaaaagc | 12 |
| 56s | tgtccctccaccccacagtggggcAAGCTTcactagggacaggattggtgacaga | 13 |
| 46s | cctccaccccacagtggggcAAGCTTcactagggacaggattggtg | 14 |
| 36s | accccacagtggggcAAGCTTcactagggacaggat | 15 |
| 106as | GGAGGAGGCCTAAGGATGGGGCTTTTCTGTCACCAATCCTGTCCCTAGTGAAGCTTGCCCCACTGTGGGGTGGAGGGGACAGATAAAAGTACCCAGAACCAGAGCC | 16 |
| 86as | TAAGGATGGGGCTTTTCTGTCACCAATCCTGTCCCTAGTGAAGCTTGCCCCACTGTGGGGTGGAGGGGACAGATAAAAGTACCCAG | 17 |
| 66as | GCTTTTCTGTCACCAATCCTGTCCCTAGTGAAGCTTGCCCCACTGTGGGGTGGAGGGACAGATAA | 18 |
| 56as | TCTGTCACCAATCCTGTCCCTAGTGAAGCTTGCCCCACTGTGGGGTGGAGGGGACA | 19 |
| 36as | ATCCTGTCCCTAGTGAAGCTTGCCCCACTGTGGGGT | 20 |

Figure 7:
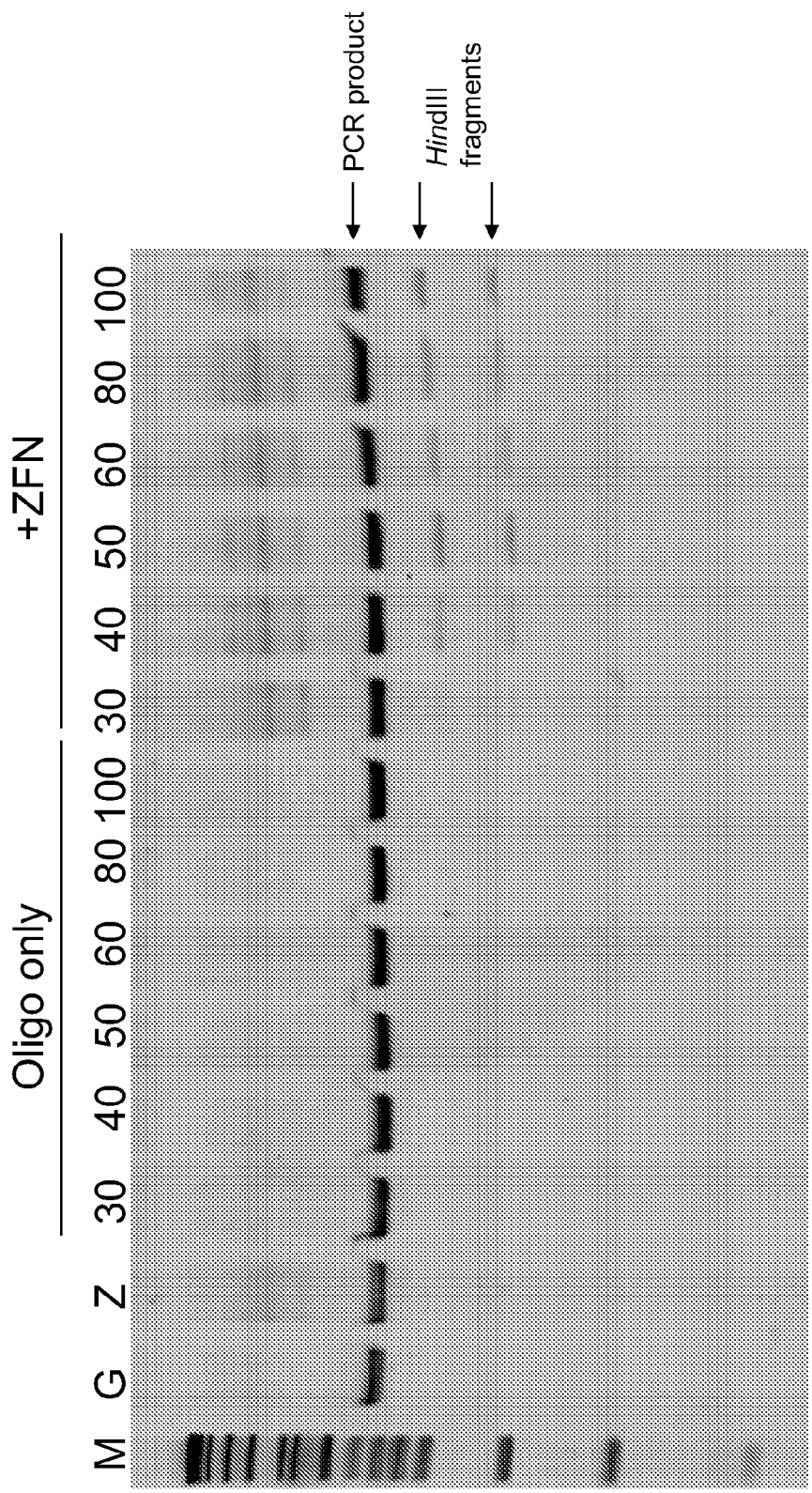
FIG. 7 illustrates integration of the HindIII site into the AAVS1 locus using sense oligonucleotides of different lengths. Genomic DNA from pools of cells was PCR amplified and digested with HindIII. Numbers along the top refer to the length in nucleotides of each oligonucleotide. M stands for markers, G stands for GFP (i.e., no ZFN control), and Z stands for ZFN.
Figure 8:
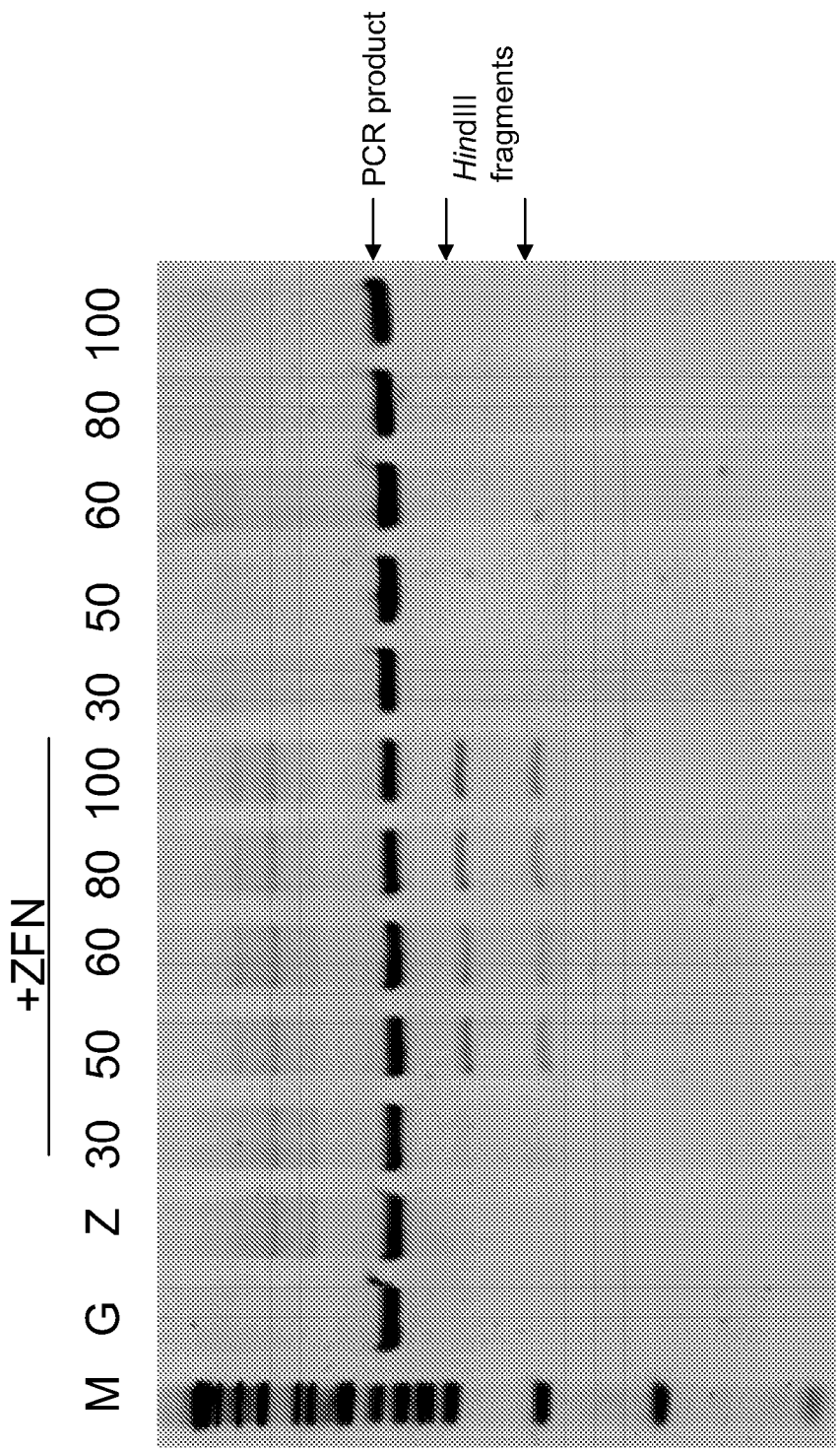
FIG. 8 depicts integration of the HindIII site into the AAVS1 locus using anti-sense oligonucleotides of different lengths. Genomic DNA from pools of cells was PCR amplified and digested with HindIII. Numbers along the top refer to the length in nucleotides of each oligonucleotide. M stands for markers, G stands for GFP (i.e., no ZFN control), and Z stands for ZFN.

K562 cells were nucleofected with 2.5 µg of plasmid DNA coding of each the AAVS1-directed ZFNs (5 µg total) and 3 µl of 100 µM oligonucleotide stock (either sense or anti-sense). Cells were harvested 2 days post nucleofection. Genomic DNA was PCR amplified and digested with HindIII. FIG. 7 presents the integration of sense strand AAVS1-HindIII oligonucleotides of varying lengths. Delivery of ZFNs and any of the oligonucleotides resulted in integration. However, oligonucleotides comprising 40 or more nt appeared to result in better integration. The integration of anti-sense strand AAVS1-HindIII oligonucleotides of varying lengths is shown in FIG. 8. As above, exposure to any of the oligonucleotides and the ZFNs resulted in integration. These data reveal that either sense or anti-sense oligonucleotides may be used, and that oligonucleotides as short as 30 nt are integrated.

Figure 9:
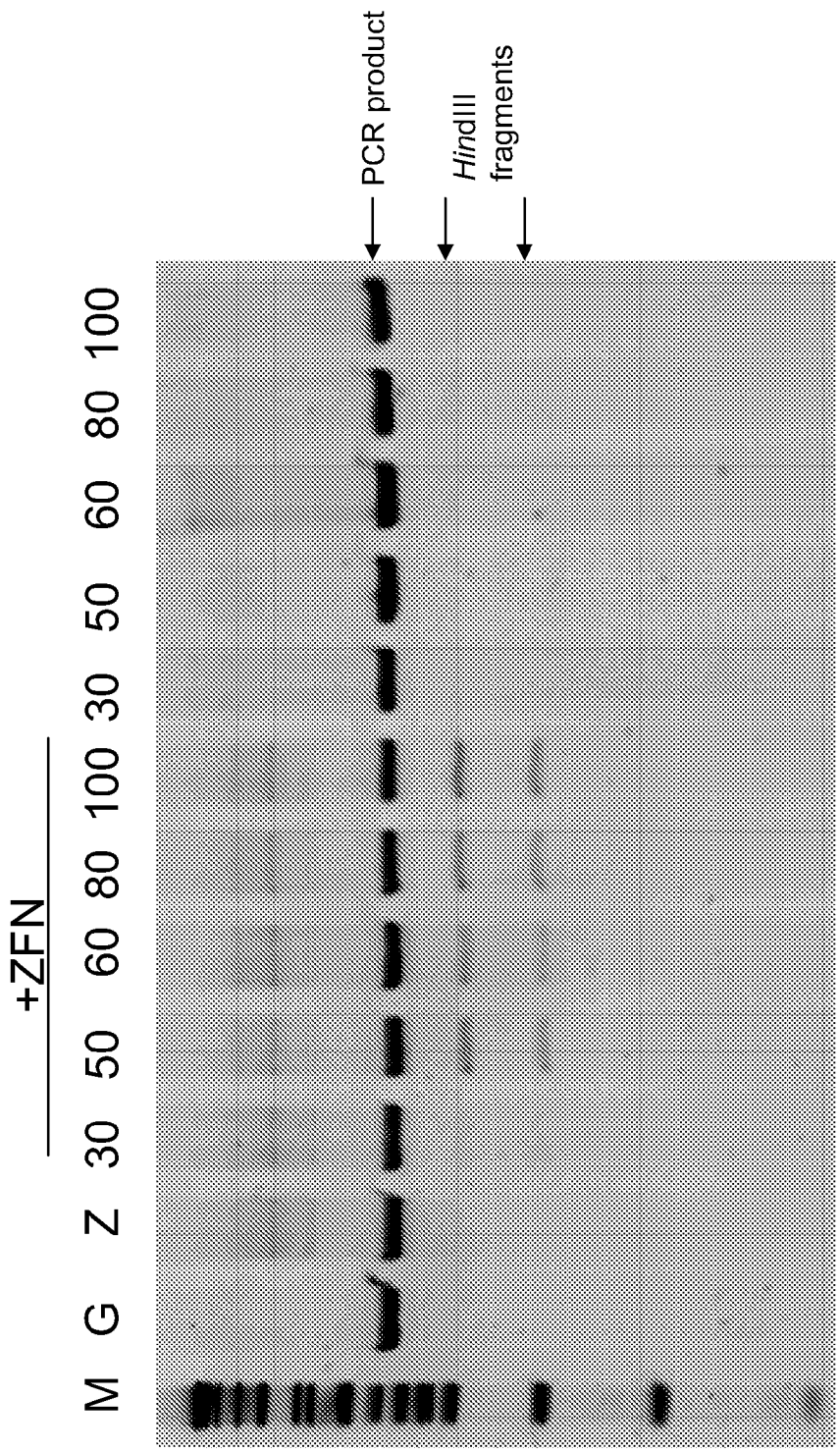
FIG. 9 shows integration of the HindIII site into the AAVS1 locus when ZFNs were delivered as mRNA or DNA in combination with oligonucleotides of different lengths. Genomic DNA from pools of cells was PCR amplified and digested with HindIII. Numbers along the top refer to the length in nucleotides of each oligonucleotide. R stands for RNA, D stands for DNA, M stands for markers, G stands for GFP (i.e., no ZFN control), and Z stands for ZFN.

To determine whether the type of nucleic acid encoding the ZFNs affected the rate of insertion, K562 cells were nucleofected with 2.5 µg DNA or 2.0 µg of mRNA encoding each ZFN (5 µg or 4 µg total, respectively) and 3 µl of 100 µM AAVS1-HindIII oligonucleotide (i.e., 50, 60, or 100 nt). Cells were harvested 2 days post nucleofection. Genomic DNA was PCR amplified and digested with HindIII. As shown in FIG. 9, delivery of ZFNs as RNA resulted in better integration of the oligonucleotides having different lengths.

Figure 10:
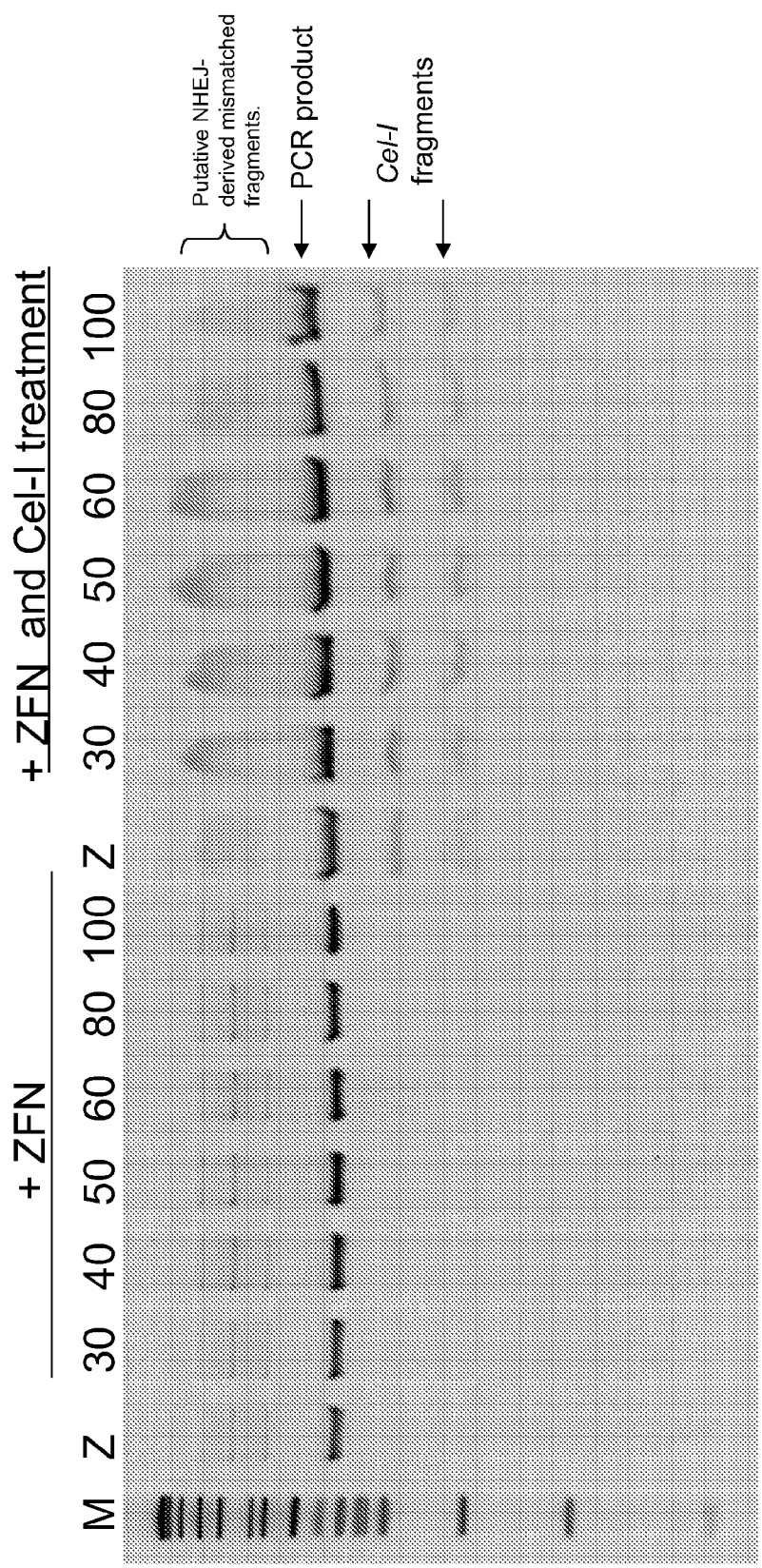
FIG. 10 depicts a Cel-1 assay of cells comprising the HindIII site at the AAVS1 locus. Numbers along the top refer to the length in nucleotides of each oligonucleotide. M stands for markers, G stands for GFP (i.e., no ZFN control), and Z stands for ZFN.

To detect putative NHEJ fragments, ZFN/oligonucleotide-treated cells were subjected to a Cel-1 assay. The Cel-1 assay detects alleles of the target locus that deviate from wild type as a result of NHEJ-mediated imperfect repair of ZFN-induced DNA double strand breaks and/or insertion of additional nucleotides. PCR amplification of the targeted region from a pool of ZFN-treated cells generates a mixture of WT and mutant amplicons. Melting and reannealing of this mixture results in mismatches forming between heteroduplexes of the WT and mutant alleles. A DNA "bubble" formed at the site of mismatch is cleaved by the surveyor nuclease Cel-1, and the cleavage products can be resolved by gel electrophoresis. The relative intensity of the cleavage products compared with the parental band is a measure of the level of Cel-1 cleavage of the heteroduplex. For this, pools of ZFN/oligonucleotide-treated cells were PCR amplified and divided into two samples. One sample was left untreated and the other sample was treated with 1 μl Cel-1 enzyme and 1 μl of enhancer for 30 minutes at 42° C. The results are presented in FIG. 10. Cel-1 fragments and putative NHEJ-derived mismatched fragments were detected in the Cel-1 treated cells.

Example 4

Homology is Required for Oligonucleotide-Mediated Integration

Figure 11:
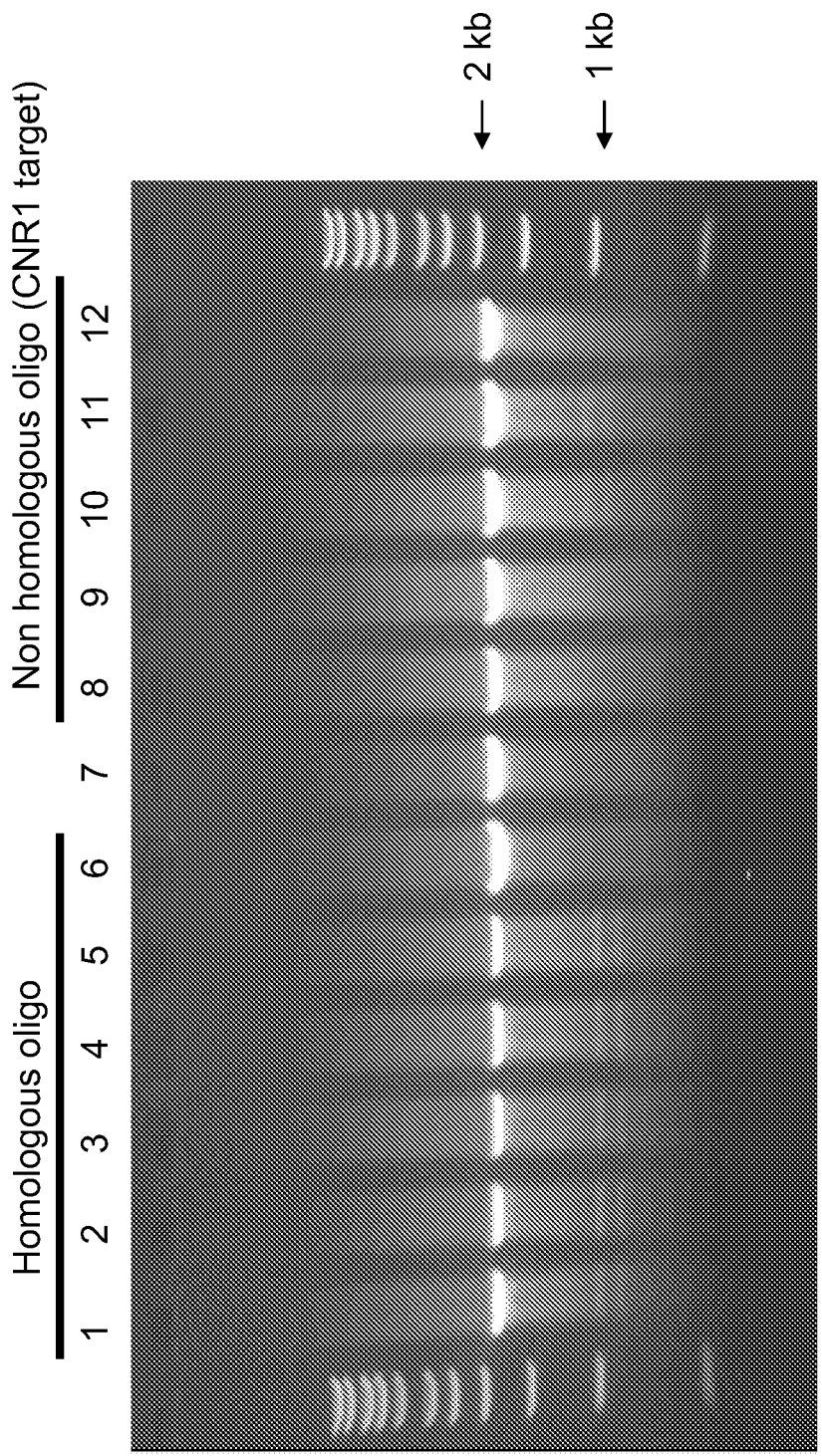
FIG. 11 illustrates the use of homologous versus non-homologous oligonucleotides for integration of the HindIII site at the AAVS1 locus. 1, 8=sense, single-stranded; 2, 9,=anti-sense, single-stranded; 3, 10=sense plus anti-sense; 4=sense, single-stranded (2×); 5, 11=double-stranded (pre-annealed); 6, 12=oligonucleotide alone (no ZFN), and 7=wild-type.

A549 cells were nucleofected with 4 μg of mRNA encoding AAVS1-targeted ZFNs and either an AAVS1-Hind III oligonucleotide or a CNR1-Hind III oligonucleotide. For each type of oligonucleotide the following forms were tested: a) sense, single-stranded; b) anti-sense single-stranded; c) sense plus antisense; d) sense single-stranded (2×); e) double-stranded (pre-annealed). After two days of incubation, cells were harvested, genomic DNA was PCR amplified, and then digested with HindIII. As shown in FIG. 11, only cells exposed to the homologous AAVS1-HindIII oligonucleotide had a HindIII site in the AAVS1 locus.

Example 5

Targeted Genomic Deletion in Cells with ssDNA Oligos and ZFNs

To determine whether single-stranded DNA oligonucleotides (ssODN, single-stranded oligodeoxynucleotide) could be used to delete a targeted genomic sequence of 0.1 kb-100 kb at the AAVS1 locus in K562 cells, a number of ssODNs were prepared. ssODNs designed to delete 5 kb, 10 kb and 100 kb targeted AAVS1 genomic sequence are presented in Table 2. Each oligonucleotide contained a region (designated I' in FIG. 12) with sequence identity to a genomic region (i.e., the distal deletion border or deletion endpoint region) located a specified distance from the ZFN cut site and a region (designated II in FIG. 12) corresponding to the appropriate ZFN binding site near the ZFN cut site. The oligonucleotides were made using standard synthesis procedures (e.g. no chemical modifications) and were PAGE purified.

12 illustrates deletions 5' to the ZFN cut site. Panel B of FIG. 12 illustrates deletion 3' to the ZFN cut site.

Targeted genomic DNA deletion of different sizes at the AAVS1 locus in K562 with single-stranded oligonucleotide and ZFN. K562 cells were nucleofected with 4 μg of mRNA coding the AAVS1-directed ZFNs (8 μg total) and 3 μl of 100 μM ssODN donor: AAVS1-0.1 kb, AAVS1-0.5 kb, AAVS1-1 kb, AAVS1-1.5 kb, AAVS1-2 kb AAVS1-2.5 kb, AAVS1-3 kb, AAVS1-3.5 kb, AAVS1-4 kb, AAVS1-4.5 kb, AAVS1-5 kb, AAVS1-10 kb, AAVS1-10.2 kb, AAVS1-19.9 kb AAVS1 -20 kb, AAVS1-50 kb, AAVS1-100 kb. K562 cells nucleofected with ssODN only, or with ZFN only were used as control. K562 cells were harvested 2 days post nucleofection, Genomic DNA was PCR amplified by a forward primer upstream of the 5' end of the distant deletion end point, and a reverse primer downstream of the 3' end of the right binding site of the ZFN, as shown in panel A of FIG. 12. Similarly, using the ZFN cut site as the reference point, for the scheme of 3' deletions off the ZFN cut site in panel B of FIG. 12, the forward primer is upstream of the 5' end of the binding site of the ZFN, and reverse primer is downstream of the 3' end of the distant deletion end point.

Figure 13:
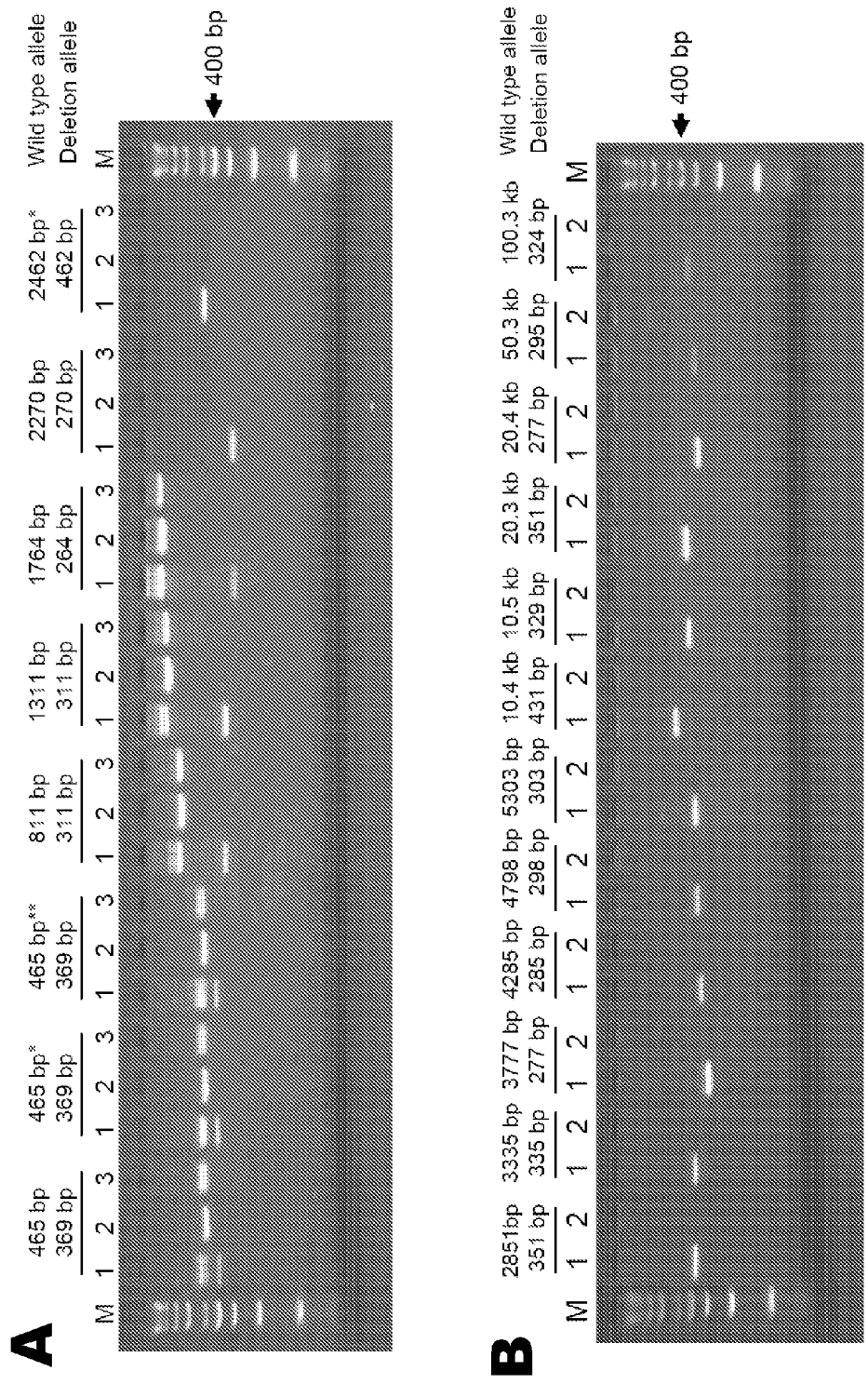
FIG. 13 depicts the PCR confirmation of the targeted genomic DNA deletion at the AAVS1 locus in K562 with single-stranded oligonucleotides and ZFNs. Lanes labeled as "1" used K562 cells exposed to both the oligonucleotide and ZFN, and thus the PCR fragments were derived from the deletion allele. Lanes labeled as "2" used K562 cells exposed only to oligonucleotide but without ZFN and the resultant PCR fragments are of the wild type allele (without deletion). Lanes labeled as "3" used K562 cells exposed to ZFN only, and thus the PCR products indicated the fragments of the wild type allele as well. The expected size of the wild type allele PCR fragments and the deletion allele PCR fragments are presented above each group of lanes. Panel (A) shows targeted genomic DNA deletions of about 0.1 kb, 0.5 kb, 1.0 kb, 1.5 kb, 2 kb, and 2.5 kb, and panel (B) shows targeted DNA deletions of about 3.0 kb, 3.5 kb, 4.0 kb, 4.5 kb, 5.0 kb, 10.0 kb, 10.2 kb, 20.0 kb, 20.2 kb, 50 kb and 100 kb using single stranded oligonucleotides. Among the groups of lanes, groups with an asterisk "*" indicated 3' deletion off the ZFN cut site; groups without asterisk "*" indicated 5' deletion off the ZFN cut site; the one group with double asterisk "**" indicated both the 5' and 3' deletion off the ZFN cut site. "M" stands for DNA marker.

In FIG. 13, lanes labeled as "2" used K562 cells exposed only to oligonucleotide but without ZFN as a template for PCR amplification. Therefore the PCR fragments were expected to have a size indicative of being derived from the wild type allele (without deletion). Lanes labeled as "3" used K562 cells exposed to ZFN only, and thus the PCR products were expected to also have the length indicative of being derived from the wild type allele (or NHEJ products). Lanes labeled as "1" used K562 cells exposed to both the oligonucleotide and ZFN, and thus the PCR fragments were expected to be amplified from the deletion allele, and therefore smaller in size than the wild type allele by the number of base pairs designed to be deleted. Depending on the intended deletion lengths in the cell, Lane 1 may also comprise PCR fragments amplified from the wild type allele. The expected size of the wild type allele PCR fragments and the deletion allele PCR fragments are presented above each group of lanes in FIG. 13. The PCR fragments were all of expected size, indicating that the targeted genomic DNA deletion of about 0.1 kb, 0.5 kb, 1.0

TABLE 2

| ssODN donor | Sequence | SEQ ID NO |
| --- | --- | --- |
| AAVS1-5 kb | 5'*ATAAGCAGGTGAAGTTAGAACATCCACAAAAGTA TAAAATTGACTCTTCTGTCCTGTGTG*<u>CTAGGGACAGGATT</u>GGT GACAGAAAAGCCCCATCCTTAGG3' | 21 |
| AAVS1-10 kb | 5'*AGGAGAATTGTAGGTTCAAGAGACCATGTTGT AACAGGTGGGTGATAACAGGCTTTAA*<u>CTAGGGACAGGATT</u>GGT GACAGAAAAGCCCCATCCTTAGG3' | 22 |
| AAVS1-100 kb | 5'*TACCCAAAGAAGCTTCTTCCACTCTGATAAAAGA AAGGAAAAATAGGCAAAGCCACAGAC*<u>CTAGGGACAGGATT</u>GGT GACAGAAAAGCCCCATCCTTAGG3' | 23 |

In the exemplary ssODN sequences presented in Table 2 above, underlined are nucleic acids in the locus comprising the ZFN binding site (the region designated as II in FIG. 12). The nucleic acids with both underline and in bold are the recognition nucleotides for the right binding site of the AAVS1 ZFNs. The nucleic acids in bold-italic but without underline are complementary to the distant deletion end point (the region designated as I in FIG. 12. Panel A of FIG.

kb, 1.5 kb, 2 kb, 2.5 kb, 3.0 kb, 3.5 kb, 4.0 kb, 4.5 kb, 5.0 kb, 10.0 kb, 10.2 kb, 19.9 kb, 20 kb, 50 kb and 100 kb using single stranded oligonucleotides and ZFN were successfully performed.

Using ZFN cut site as a reference point, according to the selection of the upstream (for 3' deletion) and/or downstream (5' deletion) ZFN cut site(s) relative to the targeted genomic deletion region, antisense and/or sense single strand oligonucleotides were used to mediate the targeted genomic deletion, specifically upstream ZFN cut site. In FIG. 13, among the groups of lanes, groups with an asterisk "*" indicated 3' deletion off the ZFN cut site; groups without asterisk "*" indicated 5' deletion off the ZFN cut site; the one group with double asterisk "**" indicated both the 5' and 3' deletion off the ZFN cut site. As shown in FIG. 13, each type of the groups showed to have PCR products with expected size.

Figure 14:
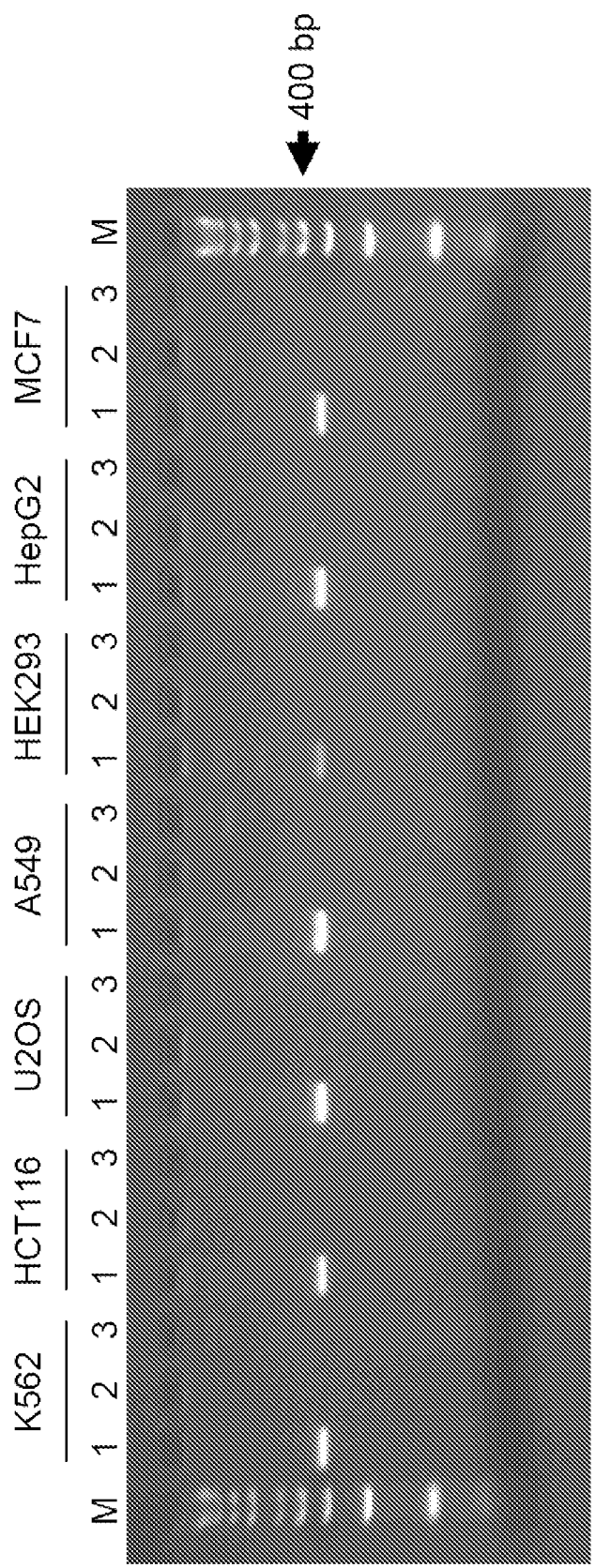
FIG. 14 presents the PCR confirmation of targeted 5 kb genomic DNA deletion at the AAVS1 locus in different cell types with single-stranded oligonucleotides and ZFNs. Deletion allele PCR fragments in all cell samples including K562, HCT116, U2OS, A549, HEK293, HepG2 and MCF7 cells have the expected size of 303 bp. "1" stands for "oligonucleotide+ZFN"; "2" stands for "oligonucleotide only"; "3" stands for "ZFN only"; and "M" stands for DNA marker. The expected wild type allele PCR fragment is 5303 bp, and the expected deletion allele PCR fragment is 303 bp.

Targeted 5 kb genomic DNA deletion at the AAVS1 locus in different cell types with single-stranded oligonucleotide and ZFN. To test targeted genomic DNA deletion at the AAVS1 locus in different cells, each of the K562, HCT116, U20S, A549, HEK293, HepG2 and MCF7 cell pools were nucleofected with 4 µg of mRNA coding the AAVS1-directed ZFNs (8 µg total) and 3 µl of 100 µM ssODN donor: AAVS1-5 kb. Each of the cell pools nucleofected with ssODN only, or with ZFN only was used as control. Cells were harvested 2 days post nucleofection. Genomic DNAs were PCR amplified by forward primer upstream of the 5' end of the targeted deletion and reverse primer downstream of the 3' end of the targeted deletion. The lanes labeled as "1" used DNA from cells exposed to both the oligonucleotide and ZFN as PCR template, and the PCR fragments were expected to be amplified from the deletion allele, with a size 5 kb smaller than the wild type allele PCR fragment (5303 bp). As shown in FIG. 14, deletion allele PCR fragments in all cell samples had the expected size of 303 bp.

Figure 15:
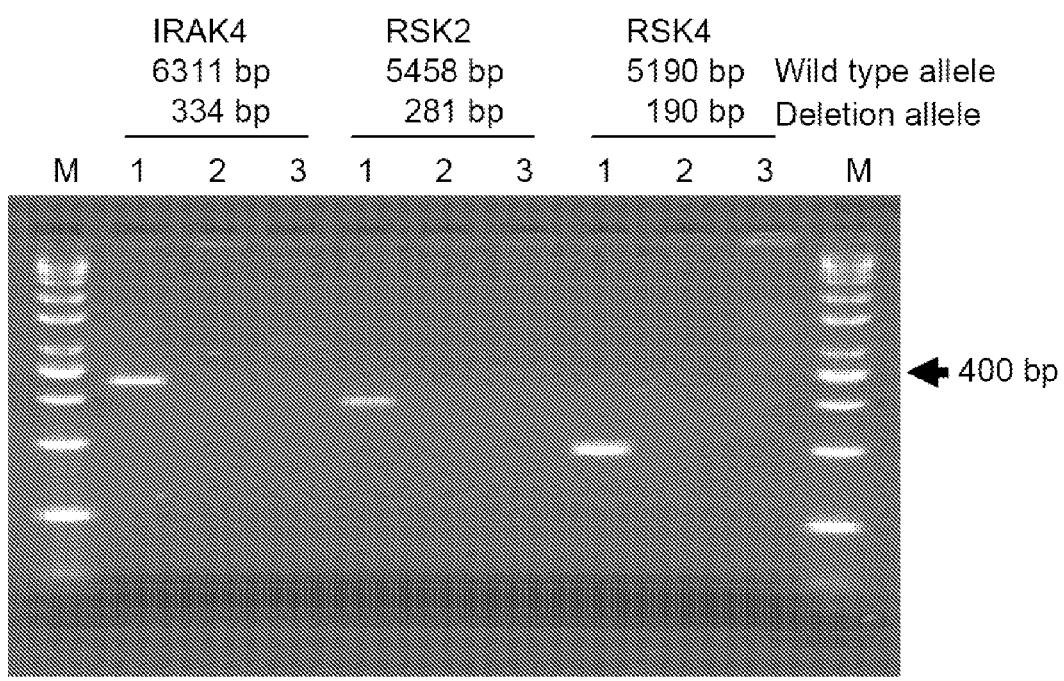
FIG. 15 depicts the PCR confirmation of targeted genomic DNA deletion at the IRK4, RSK2 and RSK4 loci in K562 with single-stranded oligonucleotides and ZFNs. The deletion allele PCR fragments in all cell samples have the expected size of 334 bp for IRAK4 locus, 281 bp for RSK2 locus, and 190 bp for RSK4 locus, respectively. "1" stands for "oligonucleotide+ZFN"; "2" stands for "oligonucleotide only"; "3" stands for "ZFN only"; and "M" stands for DNA marker.

Targeted genomic dna deletion at different loci in K562 with single-stranded oligonucleotide and ZFN. To test targeted genomic DNA deletions at the different loci in K562 cells, the K562 cells were nucleofected with each of (1) mRNA (8 µg total) coding the IRAK4-directed ZFNs and a ssODN donor (3 µl of 100 µM) for 6 kb deletion; (2)) mRNA (8 µg total) coding the RSK2-directed ZFNs and a ssODN donor (3 µl of 100 µM) for 5.2 kb deletion; and (3) mRNA (8 µg total) coding the RSK4-directed ZFNs and a ssODN donor (3 µl of 100 µM) for 5.0 kb deletion. Each of the cell pool samples nucleofected with ssODN only, or with ZFN only was used as control. Cells were harvested 2 days post nucleofection and genomic DNA isolated. Genomic DNAs were PCR amplified by forward primer upstream of the 5' end of the targeted deletion, and reverse primer downstream of the 3' end of the targeted deletion. The lanes labeled as "1" used DNA from cells exposed to both the oligonucleotide and ZFN as PCR template, and the PCR fragments were expected to be amplified from the deletion allele. As shown in FIG. 15, deletion allele PCR fragments in all cell samples had the expected size of 334 bp for IRAK4 locus, 281 bp for RSK2 locus, and 190 bp for RSK4 locus, respectively.

Precision evaluation of targeted genomic DNA deletion at AAVS1 locus in K562 with single-stranded oligonucleotide and ZFN. DNA sequence analyses of clones of genomic DNA pool were conducted to evaluate the level of precision of the targeted deletion mediated by single-stranded oligonucleotides and ZFNs. The genomic DNA pool was isolated from the K562 cells exposed to ZFN and single strand oligonucleotides designed to delete a targeted 100 bp off 5' of the ZFN cut site at the AAVS1 locus. Slightly over 40% of the clones had alleles with precise deletion of the targeted 100 bp; slightly over 55% of the clones comprised wild type alleles (without deletion, break or repair) or alleles as a result of non-homologous end-joining (NHEJ); and the clones having alleles with imprecise deletion (i.e., additional 81 bp deletion off the intended 5' deletion boundary) were less than 5% (data not shown).

In another event, the clones of the genomic DNA pool that was isolated after the K562 cells were exposed to ZFN and single strand oligonucleotides designed to delete a targeted 100 bp off 3' of the ZFN cut site at the AAVS1 locus were subjected to DNA sequencing analysis. Slightly over 50% of the clones had alleles with precise deletion of the targeted 100 bp; slightly under 50% of the clones comprised wild type alleles (without deletion, break or repair) or alleles as a result of non-homologous end-joining (NHEJ); and there were no clones having alleles with imprecise deletion (data not shown) (data not shown).

In yet another event, the clones of the genomic DNA pool that was isolated after the K562 cells were exposed to a pair of ZFNs across the targeted region for deletion and two sets of single strand oligonucleotides designed to delete a targeted 100 bp off both 5' and 3' of the ZFN cut sites at the AAVS1 locus were subjected to DNA sequence analysis. Over 20% of the clones had alleles with precise deletion of the targeted 100 bp off 5' of the ZFN cut site; slightly under 30% of the clones had alleles with precise deletion of the targeted 100 bp off 3' of the ZFN cut site; slightly under 50% of the clones comprised wild type alleles (without deletion, break or repair) or alleles as a result of non-homologous end-joining (NHEJ); and there were no clones having alleles with imprecise deletion either for the 5' or 3' deletion off the ZFN cut sites (data not shown).

Single cell cloning of targeted genomic DNA deletion and analysis thereof at the AAVS1 locus in K562. Isolated single cell clones were genotyped through gel analysis to determine the allele composition at the locus where the targeted genomic DNA deletion took place. The single cell clones were isolated after the K562 cells were exposed to ZFN and single strand oligonucleotides designed to delete 5 kb, 10 kb and 100 kb genomic sequence, respectively. Homozygous deletion clones were expected to have PCR fragments of one size which were derived from the two deletion alleles in the clone. Heterozygous deletion clones were expected to have the deletion allele and the wild type non-deletion allele. The wild type non-deletion allele was detected by junction PCR with primer pairs flanking each of the two deletion borders. Table 3 summarizes the results of the single clone genotyping.

TABLE 3

| Targeted Deletion Size | No. of Clones Screened | No. of Homozygous Clones | No. of Heterozygous Clones |
|---|---|---|---|
| 5 kb | 620 | 4 (0.6%) | 19 (3.1%) |
| 10 kb | 630 | 1 (0.2%) | 41 (6.5%) |
| 100 kb | 1180 | 0 | 2 (0.2%) |

Example 6

Figure 16:
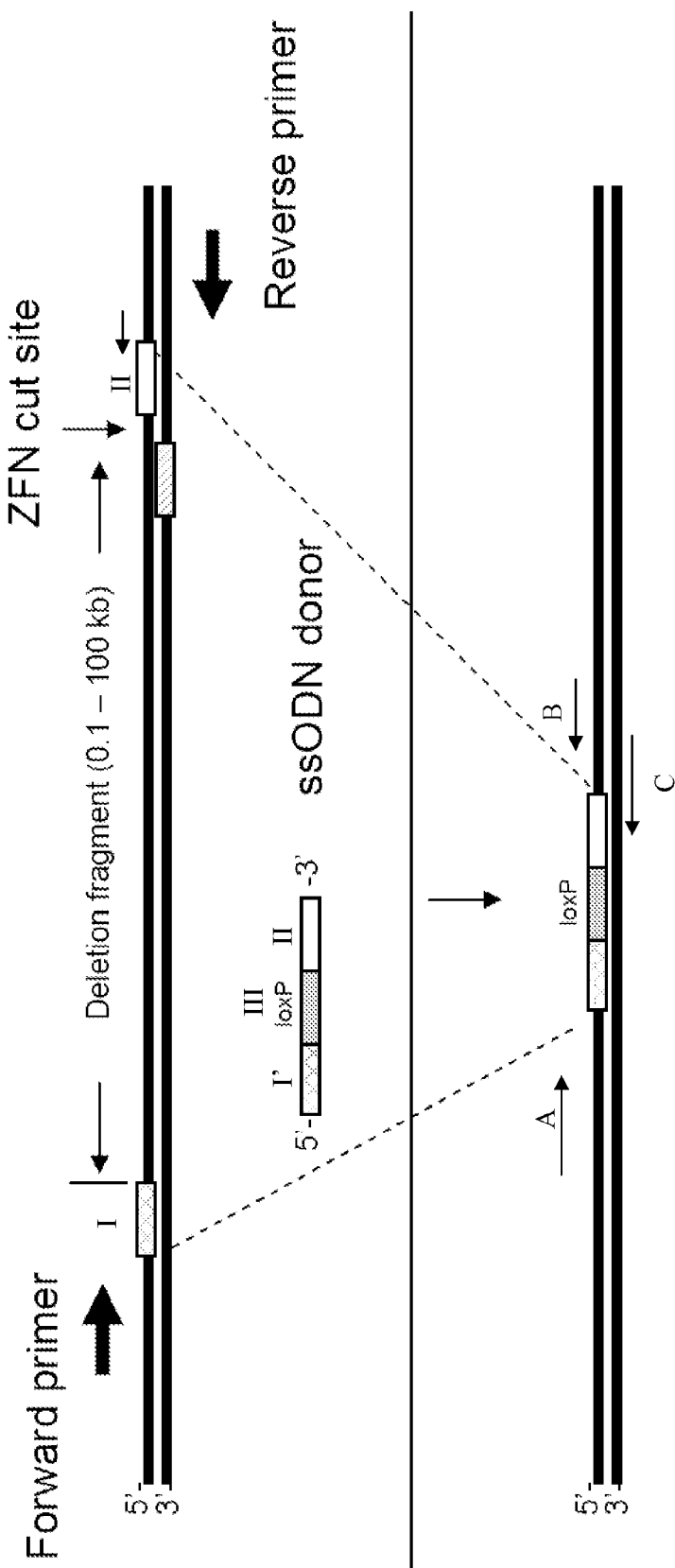
FIG. 16 illustrates an exemplary scheme to achieve simultaneous targeted genomic deletions and insertions in cells with ssDNA oligonucleotides and ZFNs. The distant deletion endpoint region is designated as I, and the ZFN binding site near the targeted cleavage site is designated as II. The ssODN donor comprises a region (designated as I') that has sequence identity to the distant deletion endpoint region, a region (designated as II) that has sequence identity to the ZFN binding site near the targeted cleavage site, and the loxP sequence (designated III). The forward primer (A) and reverse primer (B) flank regions I and II and can be used to verify the targeted deletion. Primer C comprises the nucleotides at the junction site for the ZFN right binding arm and the neighboring genomic DNA, such that forward primer (A) and reverse primer C can be used to verify the targeted insertion.

Simultaneous Targeted Genomic Deletions and Insertions in Cells With Single-Stranded DNA Oligonucleotides and ZFNs FIG. 16 illustrates an exemplary scheme to achieve simultaneous targeted genomic deletions and insertions in cells with single-stranded DNA oligonucleotides (ssODN) and ZFNs. The ssODN sequences for targeted deletion and insertion have three regions: region I' comprising nucleotide sequences complimentary to the distant deletion end point (region designated as I in FIG. 16); region II comprising the ZFN binding site nucleotide sequence (region designated as II in FIG. 16); and region III comprising the nucleotide sequence to be inserted. Specifically, oligonucleotide SM271 was designed for simultaneous targeted deletion of 5 kb and insertion of loxP site: 5' ATCCACAAAAG-TATAAAATTGACTCTTCTGTCCTGTGTGtaacttcgtatag-catacattatacgaagttat<u>CTAGGGACAGGATTGGTG-ACAGAAAAGCCCCATCCTTA</u> 3' (SEQ ID NO: 24), with loxP site represented by the nucleotide sequence in lower case, ZFN binding site underlined, recognition nucleotides for the right binding site of the ZFN underlined and in bold, and sequence complimentary to the distant deletion end point in bold-italic but without underline.

Figure 17:
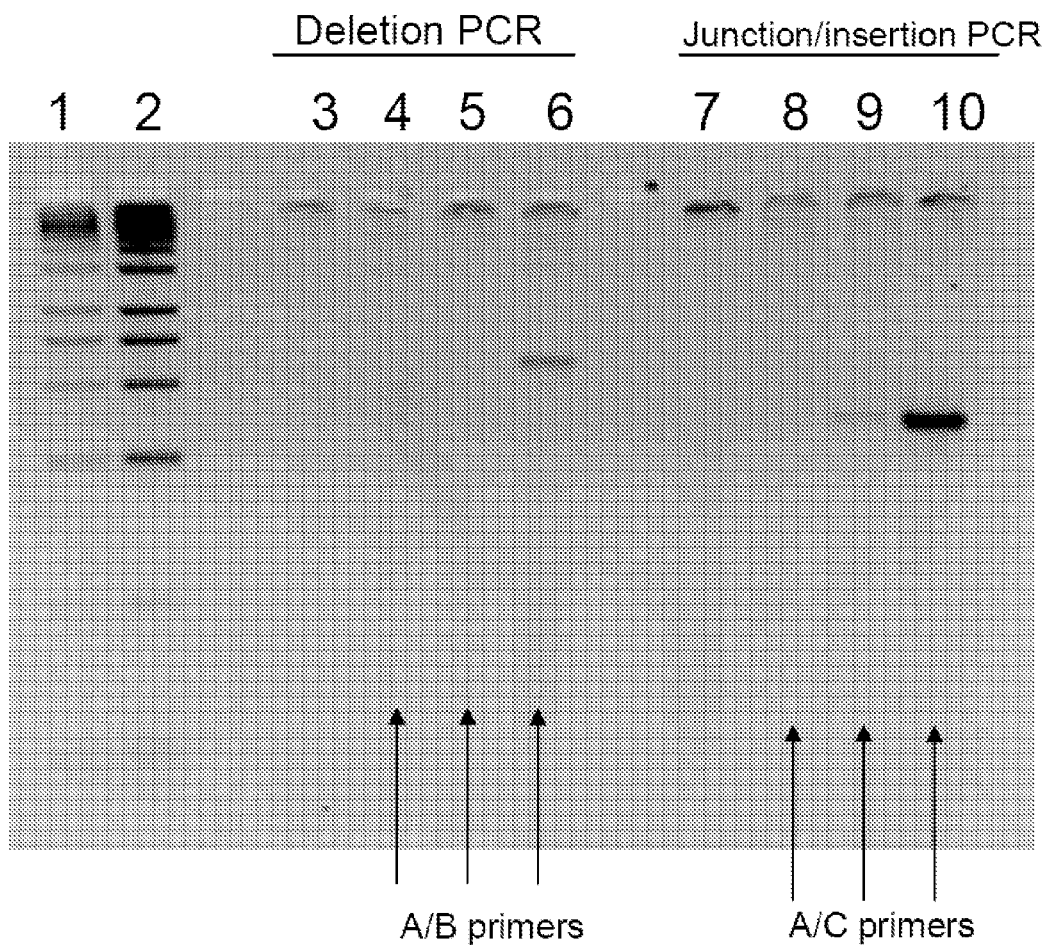
FIG. 17 shows the PCR verification of the targeted deletion of 5 kb genomic sequence that generated a 303 bp PCR fragment expected from the deletion allele (Lane 6: AAVS1-ZFN and AAVS1-5 kb ssODN) using primers A and B indicated in FIG. 16. The PCR verification of the targeted insertion of loxP sites was shown by PCR fragment with expected size in lane 10 using primers A and C. Lanes 1 and 2 represent DNA markers; lane 3 represents GFP; lane 4 represents AAVS1 ZFN (mRNA) only; lane 5 represents oligonucleotide donor only; lane 6 represents AAVS1 ZFN+ Oligonucleotide donor; lane 7 represents GFP; lane 8 represents AAVS1 ZFN (mRNA); lane 9 represents oligonucleotide donor only; lane 10 represents AAVS1 ZFN+ oligonucleotide donor.

As shown in FIG. 16, PCR forward primer A and reverse primer B that flank the regions I and II were used to verify the targeted deletion; and PCR forward primer A and reverse primer C were used to verify the targeted insertion, with primer C comprising the nucleotides at the junction site for the ZFN right binding arm and the neighboring genomic DNA. FIG. 17 shows the PCR verification of the targeted deletion of 5 kb sequence, which generated the expected 303 bp PCR fragment from the deletion allele (Lane 6: AAVS1-ZFN and AAVS1-5 kb ssODN) using primers A and B. Targeted insertion of the loxP site was verified by PCR fragment using primers A and C (FIG. 17, see lane 10).

Example 7

Figure 22:
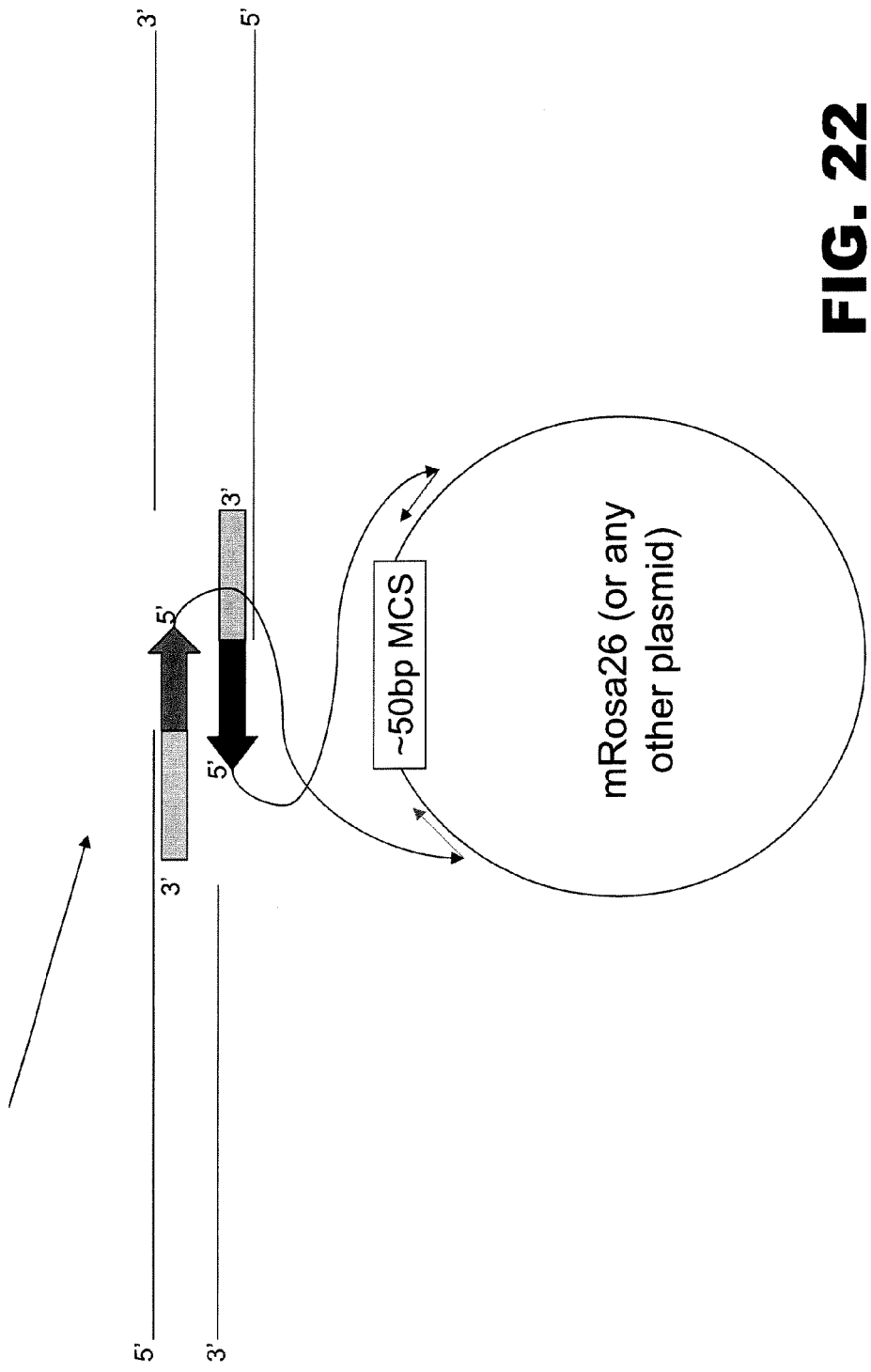
FIG. 22 presents the scheme of universal plasmid insertion methods mediated by ssDNA oligonucleotides and ZFNs. The ZFNs make double-strand breaks (DSB). The two oligonucleotide donors then bind the DSB ends using the sections that are complimentary to the ZFN cut site. Homology on 5' ends of the two oligonucleotide donors to the plasmid backbone sequence (universal or not) at either end of the desired plasmid sequence causes invasion into plasmid donor. When DSB is resolved using the donor plasmid, the desired sequence from the donor plasmid is introduced and inserted at the ZFN cut site.

Universal Plasmid Insertion Methods Mediated by Single-Stranded DNA Oligonucleotides and ZFNs The following example details the use of oligonucleotides and ZFNs to introduce a sequence of interest from a donor plasmid into the AAVS1 locus. In general, one or two ZFNs, two oligonucleotide donors, and a plasmid donor are involved in this process. The ZFNs make double-strand breaks (DSB). The two oligonucleotide donors then bind the DSB ends using the sections that are complimentary to the ZFN cut site. Each 5' end of the two oligonucleotide donors is homologous to regions in the donor plasmid (universal or not). The homology on the 5' end of the oligonucleotide donors causes invasion into the plasmid donor. When DSB is resolved using the donor plasmid, the desired sequence from the donor plasmid is introduced and inserted at the ZFN cut site (FIG. 22).

To confirm the scheme, cells were transfected with two AAVS1 ZFNs (Z), two oligonucleotide donors (O), and the mouse Rosa26 plasmid donor (D) (Z+O+D). Cells transfected with ZFNs only (Z), oligonucleotide donors only (O), plasmid donor only (D), ZFNs and oligonucleotide donors only (Z+O), ZFNs and plasmid donor only (Z+D), oligonucleotide donors and plasmid donor only (O+D) were used as controls. The transfected cells were then cultured, harvested and individual cell clones were analyzed. Junction PCR was performed to confirm the donor DNA from the plasmid donor was integrated into the AAVS1 locus. Primers AAVS1 Cel-F2 (5' TTCGGGTCACCTCTCACTCC 3'; SEQ ID NO: 25) and SM373.Junc.R1 (5' ACCTCGAGACCG-GTGGATCCGA 3'; SEQ ID NO:26) flanking the 5' junction were used for 5' junction confirmation; and primers SM373.Junc.F2 (5' GCGGTCTGAATTCGGATCCACCG 3'; SEQ ID NO: 27) and AAVS1 Cel-R2 (5' GGCTC-CATCGTAAGCAAACC 3'; SEQ ID NO: 28) flanking the 3' junction were used for 3' junction confirmation.

Figure 20A:
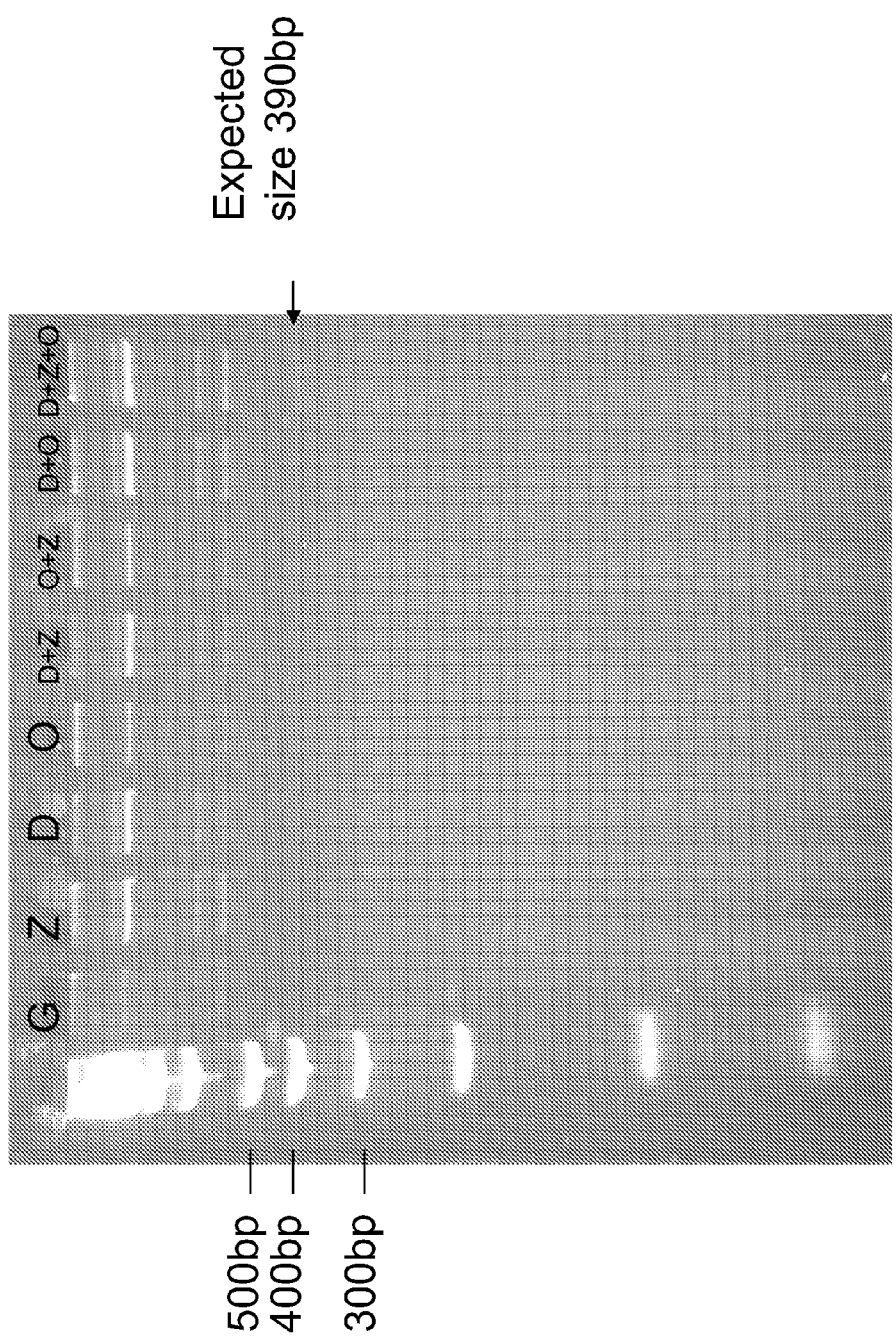
FIG. 20A shows that only the clones (Z+O+D) exposed to two ZFNs (Z), two oligonucleotide donors (O), and a plasmid donor (D) comprised the 5' junction site PCR fragment of size 390 bp that is indicative of donor sequence integration.
Figure 20B:
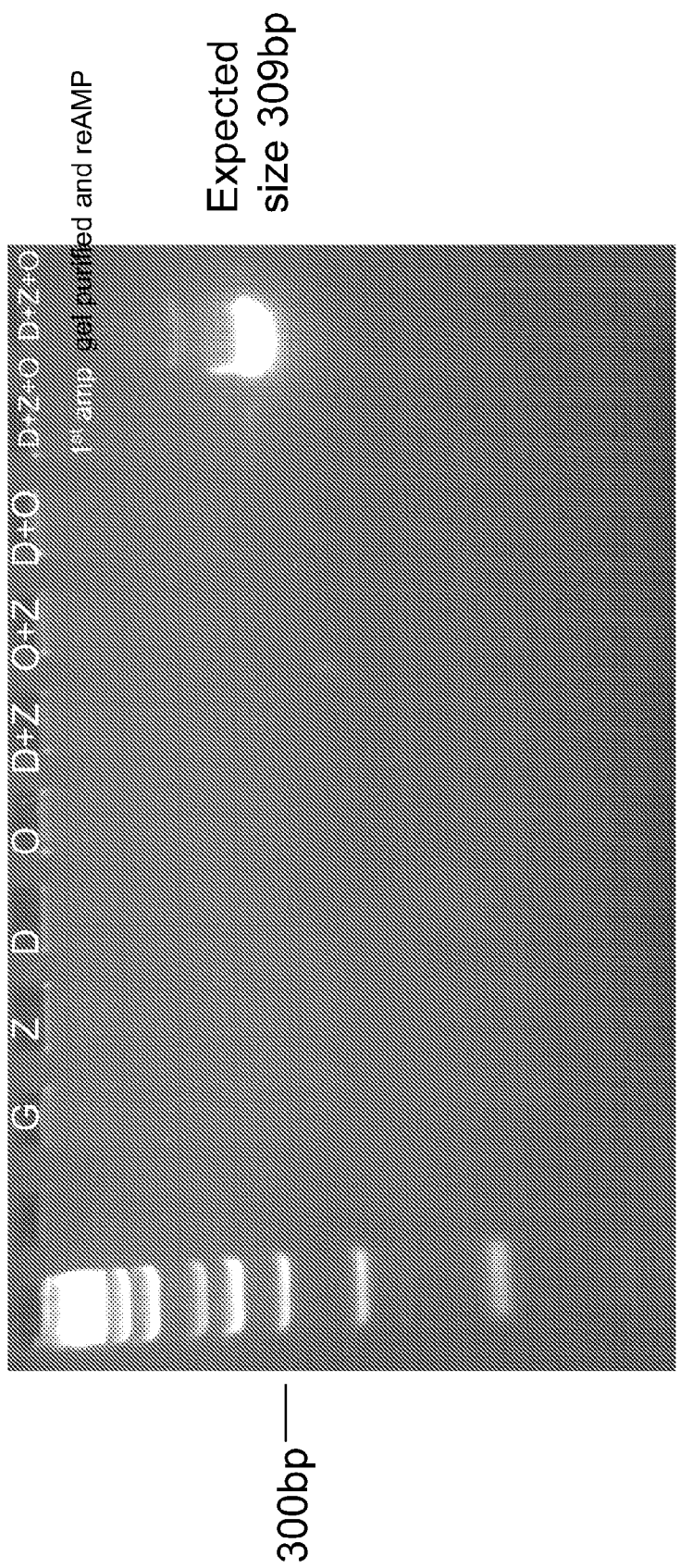
FIG. 20B shows that only the clones (Z+O+D) exposed to two ZFNs (Z), two oligonucleotide donors (O), and a plasmid donor (D) comprised the 3' junction site PCR fragment of size 309 bp, which is indicative of donor sequence integration.

Sequence analyses at the 5' junction and 3' junction confirmed that the donor sequence from the plasmid donor was integrated into the AAVS1 locus in the cells. The confirmed integration at the 5' junction is shown by the sequence presented in FIG. 18 (SEQ ID NO: 29). The confirmed integration at the 3' junction is shown by the sequence in FIG. 19 (SEQ ID NO: 30). FIGS. 20A and 20B show that the clones exposed to two ZFNs, two oligonucleotide donors, and a plasmid donor (Z+O+D) comprised the 5' junction site PCR fragment of size 390 bp (FIG. 20A) and 3' junction site PCR fragment of size 309 bp (FIG. 20B) indicative of donor sequence integration.

Example 8

Figure 21:
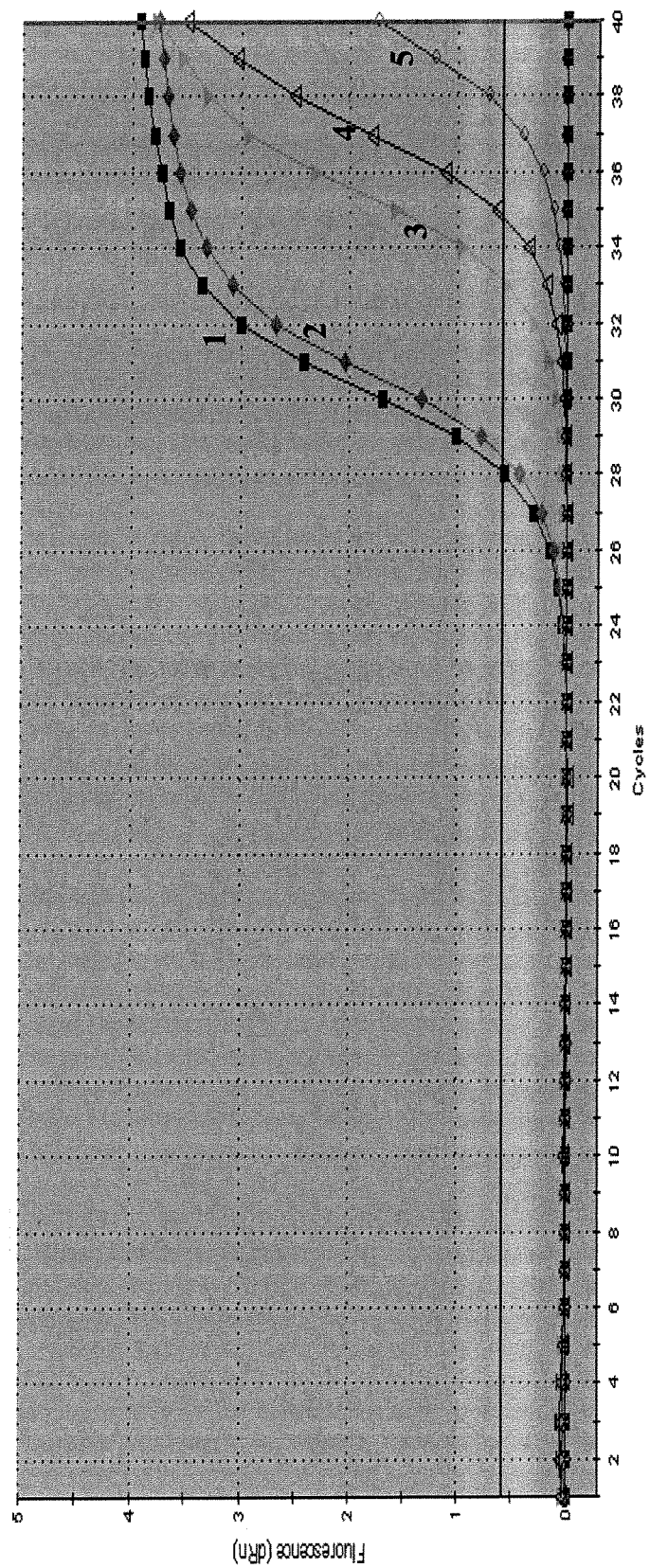
FIG. 21 depicts the relationship of oligonucleotide sequence identity (with the targeted sequence) and the efficiency of the oligo-mediated targeted deletion of a 10 kb genomic sequence. The efficiency of the 10 kb deletion was measured by SYBR Green real-time PCR. 1=100% identity; 2=98% identity; 3=90% identity; 4=50% identity; 5=negative control.

Effects of Oligonucleotide Sequence Identity on Oligo-Mediated Genome Modification of a Targeted 10 kb Genomic DNA Deletion To investigate whether sequence identity of the oligonucleotide DNA to the homologous site on the genomic sequence would affect the efficiency of the targeted genomic sequence deletion, an oligonucleotide sequence was altered on the segment corresponding to the distal deletion border 10 kb from the AAVS1 ZFN cut site, such that oligonucleotides with 100% identity, 98% sequence identity, 90% sequence identity, 50% sequence identity were prepared. The efficiency of the 10 kb deletion was then measured by SYBR Green real-time PCR (FIG. 21). The ΔCt between 100% identity and 98% identity was 0.4; the ΔCt between 100% identity and 90% identity was 5; and the ΔCt between 100% identity and 50% identity was 7. The deletion efficiency was comparable between oligonucleotides having 100% identity and oligonucleotides having 98% sequence identity. The efficiency of the deletion decreased when the sequence identity was lowered to 90%, and the efficiency was significantly lower when the sequence identity was 50% or lower.

What is claimed is:

1. A method for integrating at least one exogenous sequence into at least one chromosomal sequence in a cell, the method comprising:

a) introducing into the cell (i) at least one targeting endonuclease or nucleic acid encoding a targeting endonuclease, the targeting endonuclease being able to introduce a double-stranded break at a targeted cleavage site in the chromosomal sequence, (ii) at least one first single-stranded nucleic acid comprising a first region having substantial sequence identity to one side of the targeted cleavage site, (iii) at least one second single-stranded nucleic acid comprising a first region having substantial sequence identity to the other side of the targeted cleavage site, and (iv) at least one donor polynucleotide comprising the exogenous sequence that is flanked by a first sequence having substantial sequence identity to a second region of the first single-stranded nucleic acid and a second sequence having substantial sequence identity to a second region of the second single-stranded nucleic acid; and b) maintaining the cell under conditions such that exogenous sequence is integrated into the chromosomal sequence during repair of the double-stranded break introduced by the targeting endonuclease.

2. The method of claim 1, wherein the targeting endonuclease is a pair of zinc finger nucleases; and each of the first and second single-stranded nucleic acids is a deoxyribonucleic acid that is at least 30 nucleotides in length.

3. The method of claim 1, wherein the donor polynucleotide is a plasmid vector.

\* \* \* \* \*